US009944683B2

(12) United States Patent
Olson

(10) Patent No.: US 9,944,683 B2
(45) Date of Patent: Apr. 17, 2018

(54) CHLOROTOXIN VARIANTS, CONJUGATES, AND METHODS FOR THEIR USE

(71) Applicant: Fred Hutchinson Cancer Research Center, Se

(56) References Cited

U.S. PATENT DOCUMENTS

| | | |
|---|---|---|
| 2006/0019347 A1 | 1/2006 | Cho et al. |
| 2006/0088899 A1 | 4/2006 | Alvarez et al. |
| 2006/0166892 A1 | 7/2006 | Alvarez et al. |
| 2007/0071764 A1 | 3/2007 | Sullivan et al. |
| 2007/0154965 A1* | 7/2007 | Zhang ............ A61K 47/48261 435/7.23 |
| 2007/0237714 A1 | 10/2007 | Alvarez |
| 2007/0275902 A1 | 11/2007 | Gonda et al. |
| 2008/0153745 A1 | 6/2008 | Alvarez et al. |
| 2008/0279780 A1 | 11/2008 | Zhang et al. |
| 2009/0004105 A1 | 1/2009 | Cheng et al. |
| 2009/0123946 A1 | 5/2009 | Birkenmeyer et al. |
| 2009/0123970 A1 | 5/2009 | Tu et al. |
| 2009/0124022 A1 | 5/2009 | Birkenmeyer et al. |
| 2009/0176274 A1 | 7/2009 | Tu et al. |
| 2009/0203598 A1 | 8/2009 | McCarty et al. |
| 2009/0220430 A1* | 9/2009 | Rajopadhye ..... A61K 47/48338 424/9.6 |
| 2009/0263894 A1 | 10/2009 | Birkenmeyer et al. |
| 2009/0269777 A1 | 10/2009 | Birkenmeyer et al. |
| 2009/0304592 A1 | 12/2009 | O'Neill et al. |
| 2009/0311224 A1 | 12/2009 | Lee et al. |
| 2010/0098637 A1* | 4/2010 | Orringer ............ A61K 49/0023 424/9.1 |
| 2010/0105150 A1 | 4/2010 | Adamczyk et al. |
| 2010/0210546 A1 | 8/2010 | Alvarez et al. |
| 2010/0215575 A1 | 8/2010 | O'Neill et al. |
| 2010/0215576 A1 | 8/2010 | Sontheimer et al. |
| 2011/0027177 A1 | 2/2011 | Jacoby et al. |
| 2011/0055751 A1 | 3/2011 | Morrison et al. |
| 2011/0091380 A1 | 4/2011 | Jacoby et al. |
| 2011/0311445 A1 | 12/2011 | Alvarez et al. |
| 2012/0156131 A1 | 6/2012 | Alvarez |
| 2012/0183544 A1 | 7/2012 | Sontheimer et al. |
| 2013/0028836 A1 | 1/2013 | Sentissi et al. |
| 2013/0045163 A1 | 2/2013 | O'Neill et al. |
| 2014/0241993 A1* | 8/2014 | Zhang et al. ................. 424/9.6 |

FOREIGN PATENT DOCUMENTS

| | | |
|---|---|---|
| CN | 101270158 A | 9/2008 |
| CN | 101381405 A | 3/2009 |
| CN | 101824084 A | 9/2010 |
| CN | 101921769 A | 12/2010 |
| EP | 0155396 A2 | 9/1985 |
| EP | 1430131 B1 | 11/2005 |
| EP | 2182004 A1 | 5/2010 |
| JP | H08505615 A | 6/1996 |
| JP | H08325291 A | 12/1996 |
| JP | H0971599 A | 3/1997 |
| JP | 2002542206 A | 12/2002 |
| JP | 2005537234 A | 12/2005 |
| JP | 2008-538506 | 10/2008 |
| JP | 2009-280567 A | 12/2009 |
| JP | 2009-300110 A | 12/2009 |
| JP | 2010-085108 A | 4/2010 |
| WO | WO-8802117 A1 | 3/1988 |
| WO | WO-9311222 A1 | 6/1993 |
| WO | WO-9415576 A1 | 7/1994 |
| WO | WO 97/24619 A1 | 7/1997 |
| WO | WO-9929715 A1 | 6/1999 |
| WO | WO 00/62807 A1 | 10/2000 |
| WO | WO-0062810 A1 | 10/2000 |
| WO | WO 03/000203 A1 | 1/2003 |
| WO | WO-03008583 A2 | 1/2003 |
| WO | WO 03/101474 A1 | 12/2003 |
| WO | WO 03/101475 A1 | 12/2003 |
| WO | WO 2005/002604 A1 | 1/2005 |
| WO | WO 2005/053611 A2 | 6/2005 |
| WO | WO 2005/099774 A2 | 10/2005 |
| WO | WO 2005/107793 A2 | 11/2005 |
| WO | WO 2006/040574 A2 | 4/2006 |
| WO | WO 2006/095164 A1 | 9/2006 |
| WO | WO-2006110581 A2 | 10/2006 |
| WO | WO-2006110582 A1 | 10/2006 |
| WO | WO 2006/115633 A2 | 11/2006 |
| WO | WO-2006116156 A2 | 11/2006 |
| WO | WO 2007/044994 A2 | 4/2007 |
| WO | WO 2007/047458 A2 | 4/2007 |
| WO | WO 2007/117467 A2 | 10/2007 |
| WO | WO 2007/137163 A2 | 11/2007 |
| WO | WO 2008/088422 A2 | 7/2008 |
| WO | WO 2008/155134 A1 | 12/2008 |
| WO | WO 2009/021136 A1 | 2/2009 |
| WO | WO 2009/029760 A1 | 3/2009 |
| WO | WO 2009/049184 A2 | 4/2009 |
| WO | WO 2009/052390 A1 | 4/2009 |
| WO | WO 2009/052392 A1 | 4/2009 |
| WO | WO 2009/052400 A1 | 4/2009 |
| WO | WO 2009/062520 A1 | 5/2009 |
| WO | WO 2009/108762 A2 | 9/2009 |
| WO | WO 2009/114776 A2 | 9/2009 |
| WO | WO 2009/117018 A1 | 9/2009 |
| WO | WO 2009/133362 A2 | 11/2009 |
| WO | WO 2009/140599 A1 | 11/2009 |
| WO | WO 2009/156456 A1 | 12/2009 |
| WO | WO-2010029760 A1 | 3/2010 |
| WO | WO 2011/057295 A2 | 5/2011 |
| WO | WO 2011/094671 A2 | 8/2011 |
| WO | WO 2011/097533 A1 | 8/2011 |
| WO | WO 2011/142858 A2 | 11/2011 |
| WO | WO 2012/022742 A1 | 2/2012 |

OTHER PUBLICATIONS

Velde et al. (EJSO—European Journal of Surgical Oncology 36:6-15 Nov. 18, 2009).*

International search report and written opinion dated Apr. 8, 2014 for PCT/US2013/074215.

International search report and written opinion dated Apr. 22, 2014 for PCT/US2013/074218.

Shiue. Identification of candidate genes for drug discovery by differential display. Drug Development Research. New York. 1997; 41:142-159.

Huys, et al. Structure-function study of a chlorotoxin-chimer and its activity on Kv1.3 channels. J Chromatogr B Analyt Technol Biomed Life Sci. Apr. 15, 2004;803(1):67-73.

International search report and written opinion dated Nov. 18, 2011 for PCT/US2011/023797.

Soroceanu, et al. Use of chlorotoxin for targeting of primary brain tumors. Cancer Res. Nov. 1, 1998;58(21):4871-9.

Veiseh, et al. Tumor paint: a chlorotoxin:Cy5.5 bioconjugate for intraoperative visualization of cancer foci. Cancer Res. Jul. 15, 2007;67(14):6882-8.

Wishart, et al. 1H, 13C and 15N chemical shift referencing in biomolecular NMR. J Biomol NMR. Sep. 1995;6(2):135-40.

Akcan, et al. Chemical re-engineering of chlorotoxin improves bioconjugation properties for tumor imaging and targeted therapy. J Med Chem. Feb. 10, 2011;54(3):782-7. doi: 10.1021/jm101018r. Epub Jan. 6, 2011.

Berlier, J.E., et al., Quantitative Comparison of Long-Wavelength Alexa Fluor Dyes to Cy Dyes: Fluorscence of the Dyes and Their Bioconjugates, The Journal of Histochemistry & Cytochemistry 51(12) :1699-1712, 2003.

Butterworth, et al. Preparation of Ultrafine Silica—and PEG-Coated Magnetite Particles. Colloids and Surfaces A: Physicochemical and Engineering Aspects 179:93-102, 2001.

Citrin, et al. In vivo tumor imaging in mice with near-infrared labeled endostatin. Mol Cancer Ther. Apr. 2004;3(4):481-8.

Database Geneseq [Online] Oct. 16, 2008 (Oct. 16, 2008), "Alpha-scorpion toxin family member CTX toxin peptide analog, SEQ: 473.", XP002714000, retrieved from EBI accession No. GSP:ATD17606 Database accession No. ATD17606 * sequence.

Deshane, et al. Chlorotoxin inhibits glioma cell invasion via matrix metalloproteinase-2. J Biol Chem. Feb. 7, 2003;278(6):4135-44. Epub Nov. 25, 2002.

Egleton, R.D. and Davis, T.P., Development of Neuropeptide Drugs that Cross the Blood-Brain Barrier, J. Am. Soc. Exp. NeuroTherapeutics 2:44-53 (2005).

(56) References Cited

OTHER PUBLICATIONS

European search report and search opinion dated Oct. 15, 2013 for EP Application No. 11780950.9.
Gunn, J. et al., Smart Superparamagnetic Imaging Probes for Brain Tumor Research, in D.B. Baer and C.T. Campbell (eds.), Joint Institute for Nanoscience Annual Report, 2004, Nov. 2005, pp. 3.65-3.66.
Hockaday, D.C. et al., Imaging Glioma Extent with 131I-TM-601, J. Nuc. Med. 46(4): 580-586 (2005).
International search report and written opinion dated Oct. 6, 2010 for PCT/US2006/010170.
Jiang, T. et al., Tumor Imaging by Means of Proteolytic Activation of Cell-Penetrating Peptides, Proceedings of the National Academy of Sciences USA (PNAS) 101(51):17867-17872, Dec. 2004.
Kohler, et al. A bifunctional poly(ethylene glycol) silane immobilized on metallic oxide-based nanoparticles for conjugation with cell targeting agents. J Am Chem Soc. Jun. 16, 2004;126(23):7206-11.
Lee, M. J., et al., Rapid Pharmacokinetic and Biodistribution Studies Using Cholorotoxin-conjugated Iron oxide Nanoparticles: A Novel Non-Radioactive Method, PLoS One 5(3):e9536 1-8 (2010).
Milross, et al. Relationship of mitotic arrest and apoptosis to antitumor effect of paclitaxel. J Natl Cancer Inst. Sep. 18, 1996;88(18):1308-14.
Office action dated Mar. 24, 2010 for U.S. Appl. No. 11/897,721.
Office action dated Sep. 15, 2009 for U.S. Appl. No. 11/897,721.
Sun, et al. Size-controlled synthesis of magnetite nanoparticles. J Am Chem Soc. Jul. 17, 2002;124(28):8204-5.
Tatikolov, A.S. and Costa, S.M.B., Complexation of polymethine dyes with human serum albumin: a spectroscopic study, Biophys. Chem. 107:33-49 (2004).
Tytgat, et al. Purification and partial characterization of a 'short' insectotoxin-like peptide from the venom of the scorpion Parabuthus schlechteri. FEBS Lett. Dec. 28, 1998;441(3):387-91.
Veiseh, et al. Specific targeting of brain tumors with an optical/magnetic resonance imaging nanoprobe across the blood-brain barrier. Cancer Res. Aug. 1, 2009;69(15):6200-7. doi: 10.1158/0008-5472.CAN-09-1157. Epub Jul. 28, 2009.
Veiseh, O., et al., Optical and MRI Multifunctional nanoprobe for Targeting Gliomas, Nano Letters 5(6):1003-1008, 2005.
Weissleder, et al. Shedding light onto live molecular targets. Nat Med. Jan. 2003;9(1):123-8.
Zhang et al., Surface Modification of Superparamagnetic magnetite Nanoparticles and Their Intracellular Uptake, Biomaterial 23:1553 15-61, 2002.
Notice of allowance dated Nov. 15, 2013 for U.S. Appl. No. 11/897,721.
Notice of allowance dated Mar. 11, 2014 for U.S. Appl. No. 11/897,721.
Alander, et al. A review of indocyanine green fluorescent imaging in surgery. Int J Biomed Imaging. 2012;2012:940585. doi: 10.1155/2012/940585. Epub Apr. 22, 2012.
Kraft, et al. Interactions of indocyanine green and lipid in enhancing near-infrared fluorescence properties: the basis for near-infrared imaging in vivo. Biochemistry. Mar. 4, 2014;53(8):1275-83. doi: 10.1021/bi500021j. Epub Feb. 17, 2014.
Licha, et al. Hydrophilic cyanine dyes as contrast agents for near-infrared tumor imaging: synthesis, photophysical properties and spectroscopic in vivo characterization. Photochem Photobiol. Sep. 2000;72(3):392-8.
Marshall, et al. Near-Infrared Fluorescence Imaging in Humans with Indocyanine Green: A Review and Update. Open Surg Oncol J. 2010;2(2):12-25.
Office action dated Jul. 1, 2016 for U.S. Appl. No. 14/273,374.
Ogawa, et al. In vivo molecular imaging of cancer with a quenching near-infrared fluorescent probe using conjugates of monoclonal antibodies and indocyanine green. Cancer Res. Feb. 15, 2009;69(4):1268-72. doi: 10.1158/0008-5472.CAN-8-3116. Epub Jan. 27, 2009.

Ohnishi, et al. Organic alternatives to quantum dots for intraoperative near-infrared fluorescent sentinel lymph node mapping. Mol Imaging. Jul. 2005-Sep;4(3):172-81.
Parungo, et al. Intraoperative identification of esophageal sentinel lymph nodes with near-infrared fluorescence imaging. J Thorac Cardiovasc Surg. Apr. 2005;129(4):844-50.
Schaafsma, et al. The clinical use of indocyanine green as a near-infrared fluorescent contrast agent for image-guided oncologic surgery. J Surg Oncol. Sep. 1, 2011;104(3):323-32. doi: 10.1002/jso.21943. Epub Apr. 14, 2011.
Shimizu, et al. Development of novel nanocarrier-based near-infrared optical probes for in vivo tumor imaging. J Fluoresc. Mar. 2012;22(2):719-27. doi: 10.1007/s10895-011-1007-z. Epub Nov. 10, 2011.
Swart, et al. Homing of negatively charged albumins to the lymphatic system: general implications for drug targeting to peripheral tissues and viral reservoirs. Biochem Pharmacol. Nov. 1, 1999;58(9):1425-35.
Tanaka, et al. Image-guided oncologic surgery using invisible light: completed pre-clinical development for sentinel lymph node mapping. Ann Surg Oncol. Dec. 2006;13(12):1671-81. Epub Sep. 29, 2006.
Troyan, et al. The FLARE intraoperative near-infrared fluorescence imaging system: a first-in-human clinical trial in breast cancer sentinel lymph node mapping. Ann Surg.Oncol. Oct. 2009;16(10):2943-52. doi: 10.1245/s10434-009-0594-2. Epub Jul. 7, 2009.
Adelstein, et al. Radiotoxicity of iodine-125 and other auger-electron-emitting radionuclides: background to therapy. Cancer Biother Radiopharm. Jun. 2003;18(3):301-16.
Akabani, et al. Dosimetry and radiographic analysis of 131I-labeled anti-tenascin 81C6 murine monoclonal antibody in newly diagnosed patients with malignant gliomas: a phase II study. J Nucl Med. Jun. 2005;46(6):1042-51.
Akabani, et al. Dosimetry of 131I-labeled 81C6 monoclonal antibody administered into surgically created resection cavities in patients with malignant brain tumors. J Nucl Med. Apr. 1999;40(4):631-8.
Amersham Biosciences. CyDye Mono-reactive NHS Esters: Reagents for the labelling of biological compounds with Cy monofunctional dyes. Amersham Biosciences, 2002 20 pages.
Amersham Biosciences. Labelling of proteins with CyDye N-hydroxysuccinimide esters for fluorescent applications on the LEADseeker homogeneous imaging system. Amersham Biosciences, Jan. 2001, Issue No. L8, 4 pages.
Appelbaum, et al. Treatment of malignant lymphoma in 100 patients with chemotherapy, total body irradiation, and marrow transplantation. J Clin Oncol. Sep. 1987;5(9):1340-7.
Baker, et al. Effects of a epithelial Cl channel blocker on whole cell voltage clamp and patch clamp recordings from a human astrocytoma in culture. Proceedings of the Physiological Society, J. Physiol., vol. 438, Feb. 15-16, 1991, 4 pages.
Banks, et al. Delta sleep-inducing peptide crosses the blood-brain-barrier in dogs: some correlations with protein binding. Pharmacol Biochem Behav. Nov. 1982;17(5):1009-14.
Banks, William A. Characteristics of compounds that cross the blood-brain barrier. BMC Neurol. 2009; 9(Suppl 1): S3. Published online Jun. 12, 2009. doi: 10.1186/1471-2377-9-S1-S3.
Berendsen, Herman. A glimpse of the Holy Grail? Science. Oct. 23, 1998;282(5389):642-3.
Berezin, et al. Rational approach to select small peptide molecular probes labeled with fluorescent cyanine dyes for in vivo optical imaging. Biochemistry. Apr. 5, 2011;50(13):2691-700. doi: 10.1021/bi2000966. Epub Mar. 8, 2011.
Bertolini, et al. Inhibition of angiogenesis and induction of endothelial and tumor cell apoptosis by green tea in animal models of human high-grade non-Hodgkin's lymphoma. Leukemia, Aug. 2000, vol. 14, No. 8, pp. 1477-1482.
Bigner, et al. Iodine-131-labeled antitenascin monoclonal antibody 81C6 treatment of patients with recurrent malignant gliomas: phase I trial results. J Clin Oncol. Jun. 1998;16(6):2202-12.

(56) References Cited

OTHER PUBLICATIONS

Bodey, et al. Failure of cancer vaccines: the significant limitations of this approach to immunotherapy. Anticancer Res. Jul. 2000-Aug;20(4):2665-76.
Bowie, et al. Deciphering the message in protein sequences: tolerance to amino acid substitutions. Science. Mar. 16, 1990;247(4948):1306-10.
Bradley, et al. Limits of cooperativity in a structurally modular protein: response of the Notch ankyrin domain to analogous alanine substitutions in each repeat. J Mol Biol. Nov. 22, 2002;324(2):373-86.
Brem, et al. Placebo-controlled trial of safety and efficacy of intraoperative controlled delivery by biodegradable polymers of chemotherapy for recurrent gliomas. The Polymer-brain Tumor Treatment Group. Lancet. Apr. 22, 1995;345(8956):1008-12.
Brismar, et al. Inward Rectifying Potassium Channels in Human Malignant Glioma Cells. Brain Res 480 (1-2), 249-258. Feb. 20, 1989.
Brismar, et al. Potassium and sodium channels in human malignant glioma cells. Brain Res. Feb. 20, 1989;480(1-2):259-67.
Britton, et al. Prostate cancer: the contribution of nuclear medicine. BJU International, vol. 86, Issue s1, pp. 135-142.
Burger, et al. Topographic anatomy and CT correlations in the untreated glioblastoma multiforme. J Neurosurg. May 1988;68(5):698-704.
Burgess, et al. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Buskens, et al. Adenocarcinomas of the Gastro-Esophageal Junction: A Comparative Study of the Gastric Cardia and the Esophagus with Respect to Cyclooxygenase-2 Expression. Abstract. 2003. Publishing ID: 850, Abstract ID: 101362. 1 page. Accessed on Jan. 28, 2004. URL:< http://ddw03.agora.com/planner/displayabstract.asp?presentationid=11913>.
Castro, et al. Gene therapy for Parkinson's disease: recent achievements and remaining challenges. Histol Histopathol. Oct. 2001;16(4):1225-38.
Chien, et al. The two-hybrid system: a method to identify and clone genes for proteins that interact with a protein of interest. Proc Natl Acad Sci U S A. Nov. 1, 191;88(21):9578-82.
Chui, et al. The role of potassium channels in Schwann cell proliferation in Wallerian degeneration of explant rabbit sciatic nerves. J Physiol. Jan. 1989; 408: 199-222.
Chuthapisith, et al. Annexins in human breast cancer: Possible predictors of pathological response to neoadjuvant chemotherapy. Eur J Cancer. May 2009;45(7):1274-81. doi: 10.1016/j.ejca.2008.12.026. Epub Jan. 24, 2009.
Daly, et al. Pumiliotoxin alkaloids: a new class of sodium channel agents. Abstract of Biochem Pharmacol. Jul. 15, 1990;40(2):315-26. 1 page.
Davis, C. Geoffrey. The many faces of epidermal growth factor repeats. New Biol. May 1990;2(5):410-9.
De Muralt, et al. Reactivity of antiglioma monoclonal antibodies for a large panel of cultured gliomas and other neuroectoderm derived tumors. Anticancer Res. Jan.-Feb., 1983;3(1):1-6.
Deane, et al. An alternative pathway of B cell activation: stilbene disulfonates interact with a Cl—binding motif on AEn-related proteins to stimulate mitogenesis. EurJ Immunol. May 1992;22(5):1165-71.
DeBin, et al. Chloride channel inhibition by the venom of the scorpion Leiurus quinquestriatus. Toxicon. 1991;29(11):1403-8.
DeBin, et al. Purification and characterization of chlorotoxin, a chloride channel ligand from the venom of the scorpion. Am J Physiol. Feb. 1993;264(2 Pt 1):C361-9.
Dermer, Gerald B. Another Anniversary for the War on Cancer. Nature Biotechnology 12, 320 (1994). doi:10.1038/nbt0394-320.
Dictionary.com. Definition of the word "Moiety". pp. 1-3 (last accessed Aug. 26, 2010). URL:< http://dictionary.reference.com/browse/moiety>.
Drexler, Hans G. Recent results on the biology of Hodgkin and Reed-Sternberg cells. II. Continuous cell lines. Leuk Lymphoma. Jan. 1993;9(1-2):1-25.
Eck, et al. Gene-Based Therapy. Chapter 5. Goodman & Gilman's The Pharmacological Basis of Therapeutics. 9th Edition. pp. 77-101.
Entrez Genome. ANXA2 annexin A2 [homo sapiens]. Gene ID: 302, updated on Aug. 26, 2010. Retreived on Sep. 7, 2010. URL:< http://www.ncbi.nlm.nih.gov/gene/302>.
Epstein, et al. Morphological and virological investigations on cultured Burkitt tumor lymphoblasts (strain Raji). J Natl Cancer Inst. Oct. 1966;37(4):547-59.
Evans, et al. Design of nonpeptidal ligands for a peptide receptor: cholecystokinin antagonists. J Med Chem. Jul. 1987;30(7):1229-39.
Extended European Search Report dated Apr. 6, 2010 for European Patent Application No. EP09176234.4.
Extended European Search Report dated Jul. 30, 2010 for European Patent Application No. EP09150772.3.
Extended European Search Report dated Nov. 23, 2010 for European Patent Application No. EP08837002.8.
Fauchere, Jean-Luc. Elements for the rational design of peptide drugs. Advances in Drug Research, vol. 15, Academic Press, 1986, pp. 29-69.
Fields, et al. A novel genetic system to detect protein—protein interactions. Letters to Nature. Nature 340, 245-246 (Jul. 20, 1989); doi:10.1038/340245a0.
Fiveash, et al. Safety and tolerance of multiple weekly intracavitary injections of 131I-chlorotoxin (TM-601): Preliminary results of a prospective clinical trial in patients with recurrent glioblastoma multiforme. Poster. Journal of Clinical Oncology, 2006 ASCO Annual Meeting Proceedings. Abstact No. 1555. 1 page.
Fiveash, et al. Tumor Specific Targeting of Intravenous 131I-chlorotoxin (TM-601) in Patients With Recurrent Glioma. International Journal of Radiation Oncology, ASTRO. Nov. 1, 2007, vol. 69, Issue 3, Supplement, pp. S257-S258.
Freshney, R. Ian. Culture of animal cells: a manual of basic technique. A.R. Liss, 1983.4 pages.
Friedman, et al. Temozolomide and treatment of malignant glioma. Clin Cancer Res. Jul. 2000;6(7):2585-97.
Goldstein, et al. The blood-brain barrier. Sci Am. Sep. 1986;255(3):74-83.
Gorecki, Dariusz C. Prospects and problems of gene therapy: an update. Expert Opin Emerg Drugs. Oct. 2001;6(2):187-98.
Gorman, et al. The hope and the hype. Time, 1998, 151(19):40-44.
Gray, et al. A voltage-gated chloride conductance in rat cultured astrocytes. Proc R Soc Lond B Biol Sci. Aug. 22, 1986;228(1252):267-88.
Grimes, et al. TM-601 targets human cancer cells via a phosphatidylinositol phosphate in lamellipodia, J. Clin. Oncol., ASCO Annual Meeting Proceedings Part I, Abstract 9556 (2005).
Grissimer, et al. Calcium-activated potassium channels in resting and activated human T lymphocytes. Expression levels, calcium dependence, ion selectivity, and pharmacology. J Gen Physiol. Oct. 1993;102(4):601-30.
Grossman, et al. Current management of glioblastoma multiforme. Semin Oncol. Oct. 2004;31(5):635-44.
Gura, Trisha. Systems for identifying new drugs are often faulty. Science. Nov. 7, 1997;278(5340):1041-2.
Hajjar, et al. Annexin II: a mediator of the plasmin/plasminogen activator system. Trends Cardiovasc Med. Jul. 1999;9(5):128-38.
Hamman, et al. Oral delivery of peptide drugs: barriers and developments. BioDrugs. 2005;19(3):165-77.
Hartwell, et al. Integrating genetic approaches into the discovery of anticancer drugs. Science. Nov. 7, 1997;278(5340):1064-8.
He, et al. A simple and effective "capping" approach to readily tune the fluorescence of near-infrared cyanines. Chem. Sci., 2015,6, 4530-4536. DOI: 10.1039/C5SC00348B.
Holmes, et al. Protein labeling with fluorescent probes. Methods Cell Biol. 2001;63:185-204.

(56) References Cited

OTHER PUBLICATIONS

Holsi, et al. Evidence for GABAb-receptors on cultured astrocytes of rat CNS; autoradiographic binding studies. Experimental Brain Reserach. 1990, (80), pp. 621-625.

Huang, et al. Potassium channel induction by the Ras/Raf signal transduction cascade. J Biol Chem. Dec. 9, 1994;269(49):31183-9.

International Preliminary Examination Report dated May 29, 2001 for International PCT Patent Application No. PCT/US2000/010453.

International Preliminary Report on Patentability dated Apr. 13, 2010 for International PCT Patent Application No. PCT/US2008/079547.

International Preliminary Report on Patentability dated May 29, 2006 for International PCT Patent Application No. PCT/US2004/039325.

International Preliminary Report on Patentability dated Sep. 30, 2008 for International PCT Patent Application No. PCT/2007/008309.

International Preliminary Report on Patentability dated Sep. 30, 2010 for International PCT Patent Application No. PCT/US2008/076740.

International Preliminary Report on Patentability dated Oct. 11, 2006 for International PCT Patent Application No. PCT/US2005/011523.

International Preliminary Report on Patentability dated Nov. 25, 2010 for International PCT Patent Application No. PCT/US2009/044149.

International Search Report and Written Opinion dated Jan. 9, 2009 for International PCT Patent Application No. PCT/US2008/076740.

International Search Report and Written Opinion dated Feb. 9, 2006 for International PCT Patent Application No. PCT/US2005/011523.

International Search Report and Written Opinion dated Mar. 27, 2006 for International PCT Patent Application No. PCT/US2004/039325.

International Search Report and Written Opinion dated Oct. 19, 2009 for International PCT Patent Application No. PCT/US2009/044149.

International Search Report and Written Opinion dated Nov. 20, 2007 for International PCT Patent Application No. PCT/US2007/008309.

International Search Report dated May 7, 1996 for International PCT Patent Application No. PCT/US1996/020403.

International Search Report dated Nov. 13, 2003 for International PCT Patent Application No. PCT/US2003/017410.

Jacoby, et al. Potent pleiotropic anti-angiogenic effects of TM601, a synthetic chlorotoxin peptide. Anticancer Res. Jan. 2010;30(1):39-46.

Jalonen, Tuula. Single-channel characteristics of the large-conductance anion channel in rat cortical astrocytes in primary culture. Glia.Nov. 1993;9(3):227-37.

Jianping, Z. Chinese and Foreign Sciences Yearbook. The Second Military Medical Uniersity (SMMU) Press. p. 426 (2004).

Kaiser, Jocelyn. First Pass at Cancer Genome Reveals Complex Landscape. Science Sep. 8, 2006: vol. 313, Issue 5792, pp. 1370. DOI: 10.1126/science.313.5792.1370.

Kastin, et al. Orexin A but not orexin B rapidly enters brain from blood by simple diffusion. J Pharmacol Exp Ther. Aor. 1999;289(1):219-23.

Kaye, et al. A single amino acid substitution results in a retinoblastoma protein defective in phosphorylation and oncoprotein binding. Proc Natl Acad Sci U S A. Sep. 1990;87(17):6922-6.

Kesavan, et al. Annexin A2 is a molecular target for TM601, a peptide with tumor-targeting and anti-angiogenic effects. J Biol Chem. Feb. 12, 2010;285(7):4366-74. doi: 10.1074/jbc.M109.066092. Epub Dec. 15, 2009.

Kessler, et al. Identification of the putative brain tumor antigen BF7/GE2 as the (de)toxifying enzyme microsomal epoxide hydrolase. Cancer Res. Mar. 1, 2000;60(5):1403-9.

Kimura, et al. A dual-labeled knottin peptide for PET and near-infrared fluorescence imaging of integrin expression in living subjects. Bioconjug Chem. Mar. 17, 2010;21(3):436-44. doi: 10.1021/bc9003102. Epub Feb. 4, 2010.

Kirkin, et al. Melanoma-associated antigens recognized by cytotoxic T lymphocytes. APMIS. Jul. 1998;106(7):665-79.

Klein, et al. Surface IgM-kappa specificity on a Burkitt lymphoma cell in vivo and in derived culture lines. Cancer Res. Jul. 1968;28(7):1300-10.

Kuan, et al. EGFRvIII as a promising target for antibody-based brain tumor therapy. Brain Tumor Pathol. 2000;17(2):71-8.

Kunwar, et al. Cytotoxicity and antitumor effects of growth factor-toxin fusion proteins on human glioblastoma multiforme cells. J Neurosurg. Oct. 1993;79(4):569-76.

Laumonnier, et al. Identification of the annexin A2 heterotetramer as a receptor for the plasmin-induced signaling in human peripheral monocytes. Blood 2006 107:3342-3349; doi: https://doi.org/10.1182/blood-2005-07-2840.

Lazar, et al. Transforming growth factor alpha: mutation of aspartic acid 47 and leucine 48 results in different biological activities. Mol Cell Biol. Mar. 1988;8(3):1247-52.

Lee, et al. Increased vaccine-specific T cell frequency after peptide-based vaccination correlates with increased susceptibility to in vitro stimulation but does not lead to tumor regression. J Immunol. Dec. 1, 1999;163(11):6292-300.

Levin, V.A..The place of hydroxyurea in the treatment of primary brain tumors, Database accession No. NLM1641655 (abstract), Seminars in Oncology, 19(3):34-39 (1992).

Lippens, et al. NMR sequential assignments and solution structure of chlorotoxin, a small scorpion toxin that blocks chloride channels. Biochemistry. Jan. 10, 1995;34(1):13-21.

Lynch, Patrick M. Chemoprevention with special reference to inherited colorectal cancer. Fam Cancer. 2008;7(1):59-64. Epub Aug. 7, 2007.

Lyons, et al. Chlorotoxin, a scorpion-derived peptide, specifically binds to gliomas and tumors of neuroectodermal origin. Glia. Aug. 2002;39(2):162-73.

Malinowska, et al. Recombinant chlorotoxin: An inhibitor of gastric Cl-channels. Abstract. Biophysical Journal, 66(2):A100 (1994).

Mamelak, et al. Phase 1/11 Trial of Intracavitary 1311-TM-601 in Adult Patients with Recurrent High-Grade Glioma. Astract. Neuro-Oncology online, 5:340 (2003).

Mamelak, et al. Phase I single-dose study of intracavitary-administered iodine-131-TM-601 in adults with recurrent high-grade glioma. J Clin Oncol. Aug. 1, 2006;24(22):3644-50.

Mamelak, et al. Targeted delivery of antitumoral therapy to glioma and other malignancies with synthetic chlorotoxin (TM-601). Expert Opin Drug Deliv. Mar. 2007;4(2):175-86.

McFerrin, et al. A role for ion channels in glioma cell invasion. Neuron Glia Biol. Feb. 2006;2(1):39-49.

McKie, Robin. Cancer research set back a decade: Mislabelling of samples so common that new treatments have been wrecked, warn scientists. The Observer. Jun. 10, 2001 . 4 pages.

McMichael, et al. Leukocyte Typing III, Oxford University Press, pp. 302-363 and pp. 432-469 (1987).

Mellman, Ira. Where Next for Cancer Immunotherapy? The Scientist, 20(1): 47-56 (2006).

Merck, Chemotherapy: Prevention and Treatment of Cancer: Merck Manual Home Edition, online manual, entry 'methotrexate'. 4 pages. URL:< http://www.merck.com/rnmhe/print/sec15/ch182/ch182f.html>.

Minowada, et al. Rosette-Forming Human Lymphoid Cell Lines. I. Establishment and Evidence for Origin of Thymus-Derived Lymphocytes. J Natl Cancer Inst (1972) 49 (3): 891-895. DOI: https://doi.org/10.1093/jnci/49.3.891.

Mousa, et al. Potent anti-angiogenesis efficacy of chlorotoxin and its synergistic interactions with Anti-VEGF targets. American Association for Cancer Research Annual Meeting Proceedings, Abstract #268 (2008). 1 page.

Muro, et al. Convection-enhanced and local delivery of targeted cytotoxins in the treatment of malignant gliomas. Technology in Cancer Research and Treatment. 2006. 5(3), pp. 201-213.

(56) References Cited

OTHER PUBLICATIONS

Newlands, et al. Temozolomide: a review of its discovery, chemical properties, pre-clinical development and clinical trials. Cancer Treat Rev. Jan. 1997;23(1):35-61.
Ngo, et al. Computational Complexity, Protein Structure Prediction, and the Levinthal Paradox. The Protein Folding Problem and Ternary Structure Prediction. 1994. pp. 491-494. 4 pages.
Nolting, et al. Molecular imaging probe development: a chemistry perspective. Am J Nucl Med Mol Imaging. 2012; 2(3): 273-306.
Nolting, et al. Near-Infrared Dyes: Probe Development and Applications in Optical Molecular Imaging. Curr Org Synth. Aug. 2011;8(4):521-534.
Office Action dated Jan. 8, 2010 for Canadian Patent Application No. CA2487425.
O'Neill, et al. Treatment of Metastatic Tumors. U.S. Appl. No. 61/053,651, filed May 15, 2008.
Pappas, et al. Reduction of glial proliferation by K channel blockers is mediated by changes in pH. NeuroReport. 6(1):193-196, Dec. 1994.
Pappone, et al. Blockers of voltage-gated K channels inhibit proliferation of cultured brown fat cells. Am J Physiol. Apr. 1993;264(4 Pt 1):C1014-9.
Partial European Search Report dated Apr. 8, 2010 for European Patent Application No. EP09150772.3.
Phillips, et al. Transforming growth factor-alpha-Pseudomonas exotoxin fusion protein (TGF-alpha-PE38) treatment of subcutaneous and intracranial human glioma and medulloblastoma xenografts in athymic mice. Cancer Res. Feb. 15, 1994;54(4):1008-15.
Puro, et al. Retinal glial cell proliferation and ion channels: a possible link. Invest Ophthalmol Vis Sci. Mar. 1989;30(3):521-9.
Ramakrishnan, et al. Targeting tumor vasculature using VEGF-toxin conjugates. Methods Mol Biol. 2001;166:219-34.
Ravik, Miroslay. Intracavitary Treatment of Malignant Gliomas: Radioimmunotherapy Targeting Fibronectin. Acta neurochirurgica. Supplement 88(88):77-82 . Feb. 2003.
Rawstron, et al. Quantitation of minimal disease levels in chronic lymphocytic leukemia using a sensitive flow cytometric assay improves the prediction of outcome and can be used to optimize therapy. Blood. Ki;. 1, 2001;98(1):29-35.
Reardon, et al. A pilot study: 131I-Antitenascin monoclonal antibody 81c6 to deliver a 44-Gy resection cavity boost. Neuro Oncol. Apr. 2008; 10(2): 182-189. doi: 10.1215/15228517-2007-053.
Reardon, et al. Phase II trial of murine (131)I-labeled antitenascin monoclonal antibody 81C6 administered into surgically created resection cavities of patients with newly diagnosed malignant gliomas. J Clin Oncol. Mar. 1, 2002;20(5):1389-97.
Rescher, et al. Annexins—unique membrane binding proteins with diverse functions. J Cell Sci. Jun. 1, 2004;117(Pt 13):2631-9.
Ricotti, et al. C-Kit Is Expressed in Soft Tissue Sarcoma of Neuroectodermic Origin and Its Ligand Prevents Apoptosis of Neoplastic Cells. Blood 91 (7), 2397-2405. Apr. 1, 1998.
Rousselle, et al. New advances in the transport of doxorubicin through the blood-brain barrier by a peptide vector-mediated strategy. Mol Pharmacol. Apr. 2000;57(4):679-86.
Rudinger, J. Peptide Hormones. J.A. Parsons, Ed., pp. 1-7 (1976).
Sakamoto, et al. Identification of a new outwardly rectifying Cl— channel that belongs to a subfamily of the ClC Cl—channels. J Biol Chem. Apr. 26, 1996;271(17):10210-6.
Sgouros, George. Bone marrow dosimetry for radioimmunotherapy: theoretical considerations. J Nucl Med. Apr. 1993;34(4):689-94.
Sharma, et al. The role of annexin II in angiogenesis and tumor progression: a potential therapeutic target. Curr Pharm Des. 2007;13(35):3568-75.
Shen, et al. Dosimetry of Phase I/II study of intracavitary administered I-131-TM-601 peptide in patients with recurrent high-grade glioma. 2004. vol. 60, Issue 1, Supplement, pp. S259.
Shen, et al. Patient-specific dosimetry of pretargeted radioimmunotherapy using CC49 fusion protein in patients with gastrointestinal malignancies. J Nucl Med. Apr. 2005;46(4):642-51.
Shen, et al. Practical determination of patient-specific marrow dose using radioactivity concentration in blood and body. J Nucl Med. Dec. 1999;40(12):2102-6.
Shen, et al. Radiation dosimetry of 131I-chlorotoxin for targeted radiotherapy in glioma-bearing mice. J Neurooncol. Jan. 2005;71(2):113-9.
Sigma Genosys. Custom Peptide Synthesis: Designing Custom Peptides. 2004. Sigma Genosys. Accessed Dec. 16, 2004. 2 pages. URL:< http://www.sigma-genosys.com/peptide_design.asp>.
Silva, et al. Agents That Bind Annexin A2 Suppress Ocular Neovascularization. J Cell Physiol. Nov. 2010; 225(3): 855-864. doi: 10.1002/jcp.22296.
Skolnick, et al. From genes to protein structure and function: novel applications of computational approaches in the genomic era. Trends Biotechnol. Jan. 2000;18(1):34-9.
Smith, et al. Molecular markers in head and neck squamous cell carcinoma: their biological function and prognostic significance. Ann Otol Rhino! Laryngol. Mar. 2001;110(3):221-8.
Somogyi, et al. Subcellular localization of benzodiazepine/GABAA receptors in the cerebellum of rat, cat, and monkey using monoclonal antibodies. Journal of Neuroscience Jun. 1, 1989, 9 (6) 2197-2209.
Sontheimer, Harald. Voltage-dependent ion channels in glial cells. Glia. Jun. 1994;11(2):156-72.
Soroceanu, et al. Modulation of glioma cell migration and invasion using Cl(-) and K(+) ion channel blockers. J Neurosci. Jul. 15, 1999;19(14):5942-54.
Stabin, Michael G. Mirdose: personal computer software for internal dose assessment in nuclear medicine. J Nucl Med. Mar. 1996;37(3):538-46.
Steinmeyer, et al. Cloning and functional expression of rat CLC-5, a chloride channel related to kidney disease. J Biol Chem. Dec. 29, 1995;270(52):31172-7.
Stewart, L.A. Chemotherapy in adult high-grade glioma: a systematic review and meta-analysis of individual patient data from 12 randomised trials. Lancet. Mar. 23, 2002;359(9311):1011-8.
Stupp, et al. Current and future developments in the use of temozolomide for the treatment of brain tumours. Lancet Oncol. Sep. 2001;2(9):552-60.
Sun, et al. In vivo MRI detection of gliomas by chlorotoxin-conjugated superparamagnetic nanoprobes. Small. Mar. 2008;4(3):372-9. doi: 10.1002/smll.200700784.
Sun, et al. Tumor-targeted drug delivery and MRI contrast enhancement by chlorotoxin-conjugated iron oxide nanoparticles. Nanomedicine (Lond). Aug. 2008;3(4):495-505. doi: 10.2217/17435889.3.4.495.
Supplemental Partial European Search Report dated Mar. 11, 2003 for European Patent Application No. EP00926105.
Supplementary European Search Report dated Sep. 24, 2007 for European Patent Application No. EP05763889.2.
Supplementary Partial European Search Report dated Aug. 28, 2007 for European Patent Application No. EP03731504.
Syed, et al. Angiostatin receptor annexin ll in vascular tumors including angiosarcoma. Hum Pathol. Mar. 2007;38(3):508-13. Epub Jan. 19, 2007.
Taber's Cyclopedic Medical Dictionary, F.A. Davis Company, Philadelphia, 274 (1985). 3 pages.
Tan, et al. Deduction of Functional Peptide Motifs in Scorpion Toxins. J Pept Sci 12 (6), 420-427. Jun. 2006.
Tanaka, et al. Redox regulation of annexin 2 and its implications for oxidative stress-induced renal carcinogenesis and metastasis. Oncogene. May 13, 2004;23(22):3980-9.
Tatenhorst, et al. Knockdown of annexin 2 decreases migration of human glioma cells in vitro. Neuropathol Appl Neurobiol. Jun. 2006;32(3):271-7.
Te Velde, et al. The use of fluorescent dyes and probes in surgical oncology. Eur J Surg Oncol. Jan. 2010;36(1):6-15. doi: 10.1016/j.ejso.2009.10.014. Epub Nov. 18, 2009.
The Free Dictionary. American Heritage Medical Dictionary defines the word "systemic". 2007. 1 page.
Torchilin, et al. Peptide and protein drug delivery to and into tumors: challenges and solutions. Drug Discov Today. Mar. 15, 2003;8(6):259-66.

(56) References Cited

OTHER PUBLICATIONS

Transmolecular. A Phase I Imaging and Safety Study of Intravenous 131-1-TM-601 Labeled Chlorotoxin in Patients With Recurrent or Refractory Somatic and/or Cerebral Metastatic Solid Tumors. Clinical Trials NCT00379132. 3 pages (Aug. 2006).

Uchida, et al. Localization and functional characterization of rat kidney-specific chloride channel, CIC-K1. J Clin Invest. Jan. 1995;95(1):104-13.

Ullrich, et al. Biophysical and pharmacological characterization of chloride currents in human astrocytoma cells. Am J Physiol. May 1996;270(5 Pt 1):C1511-21.

Ullrich, et al. Cell cycle-dependent expression of a glioma-specific chloride current: proposed link to cytoskeletal changes. Am J Physiol. Oct. 1997;273(4 Pt 1):C1290-7.

Ullrich, et al. Expression of voltage-activated chloride currents in acute slices of human gliomas. Neuroscience. Apr. 1998;83(4):1161-73.

Ullrich, et al. Human astrocytoma cells express a unique chloride current. Neuroreport. Apr. 10, 1996;7(5):1020-4.

UniProt Database. Accession No. P45639 (accessed 2007).

Veber, et al. The design of metabolically-stable peptide analogs. Trends in Neurosciences. vol. 8, p. 392-396, 1985.

Veiseh, et al. A ligand-mediated nanovector for targeted gene delivery and transfection in cancer cells. Biomaterials. Feb. 2009;30(4):649-57. doi: 10.1016/j.biomaterials.2008.10.003. Epub Nov. 5, 2008.

Voet, et al. Biochemistry. Second Edition. John Wiley & Sons, Inc., pp. 235-241 (1995).

Wen, et al. PTEN controls tumor-induced angiogenesis. Proc Natl Acad Sci U S A. Apr. 10, 2001;98(8):4622-7. Epub Mar. 27, 2001.

Wilson, et al. Mitogenic factors regulate ion channels in Schwann cells cultured from newborn rat sciatic nerve. J Physiol. Oct. 1993; 470: 501-520.

Woodfork, et al. Inhibition of ATP-sensitive potassium channels causes reversible cell-cycle arrest of human breast cancer cells in tissue culture. J Cell Physiol. Feb. 1995;162(2):163-71.

Written Opinion dated Oct. 22, 2007 for International PCT Patent Application No. PCT/US2006/010170.

Yasuda, et al. Identification of a tumour associated antigen in lung cancer patients with asbestos exposure. Anticancer Res. Jul. 2010;30(7):2631-9.

Ye, et al. Integrin targeting for tumor optical imaging. Theranostics. 2011;1:102-26.

Zellner, et al. Disparity in expression of protein kinase C alpha in human glioma versus glioma-derived primary cell lines: therapeutic implications. Clin Cancer Res. Jul. 1998;4(7):1797-802.

Zips, et al. New anticancer agents: in vitro and in vivo evaluation. In Vivo. Jan.-Feb., 2005;19(1):1-7.

Bernal, Alyse. Tumor Paint Brings Light to Toddler's Brain Tumor. On the Pulse (Sep. 22, 2016). Seattle Children's Hospital. Web article. 3 pages. URL: <http://pulse.seattlechildrens.org/tumor-paint-brings-light-to-toddiers-brain-tumor/>.

Butte, et al. Near-infrared imaging of brain tumors using the Tumor Paint BLZ-100 to achieve near-complete resection of brain tumors. Neurosurg Focus. Feb. 2014;36(2):E1.

\* cited by examiner

CHLOROTOXIN VARIANTS, CONJUGATES, AND METHODS FOR THEIR USE

CROSS-REFERENCES TO RELATED APPLICATIONS

This application is a continuation of International Application No. PCT/US2011/023797, filed Feb. 4, 2011, which claims the benefit of U.S. Provisional Application No. 61/333,556, filed May 11, 2010. Each application is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 40329_SEQ_Final.txt. The text file is 2.70 KB; was created on Nov. 9, 2012; and is being submitted via EFS-Web with the filing of the specification.

FIELD OF THE INVENTION

The present invention generally relates to chlorotoxin, and more particularly to chlorotoxin variants, chlorotoxin variant conjugates, compositions that include the chlorotoxin variants or conjugates, and methods for using the chlorotoxin variants, conjugates, and compositions.

BACKGROUND OF THE INVENTION

Neurosurgeons have long sought methods to illuminate brain cancer cells to identify cancer foci and distinguish cancer from normal tissue in real time during tumor resection operations. A bioconjugate composed of chlorotoxin (CTX), a peptide discovered from the *Leiurus quinquestriatus* scorpion, and near infrared fluorescent (NIRF) molecules, such as Cy5.5, ("tumor paint") clearly identifies tumor foci with high sensitivity (M. Veiseh, et al., "Tumor Paint: A Chlorotoxin:Cy5.5 Bioconjugate for Intra-Operative Visualization of Cancer Foci," *Cancer Research* 67(14): 6882-88, 2007). CTX was originally selected for these studies because it preferentially binds to glioma cells compared with normal brain tissue (L. Soroceanu, et al., "Use of Chlorotoxin for Targeting of Primary Brain Tumors," *Cancer Research* 58:4871-4879, 1998). Because the CTX target appears to be shared by multiple other cancer types, CTX: Cy5.5 effectively illuminated prostate, colon, sarcoma, medulloblastoma, and other types of solid tumors (M. Veiseh 2007).

CTX is a 36 amino acid peptide with four disulfide bridges that confer a high degree of three dimensional structure to the polypeptide. CTX has three lysine residues at positions 15, 23, and 27 that have been utilized for conjugation to NHS-ester modified Cy5.5 and other fluorescent molecules. The resultant bioconjugate is a mixture of typically 75-85% mono-labeled peptide at position 27 and lesser amounts of di- and tri-labeled peptide conjugated to Lys 15 and Lys 23. Although it is possible to have mixtures approved by the Food and Drug Administration (FDA) and similar regulatory agencies elsewhere, commercialization is potentially hindered as it is expensive and difficult to match the ratio of mono-, di- and tri-labeled batches in the future.

A need exists for a polypeptide having chlorotoxin's advantageous properties and having a single lysine residue for conjugation with diagnostic or therapeutic agents to provide a single, homogenous new molecular entity. The present invention seeks to fulfill this need and provides further related advantages.

SUMMARY OF THE INVENTION

The present invention provides chlorotoxin variants, conjugates made from the chlorotoxin variants, compositions that include the chlorotoxin variants or conjugates, and methods for using the chlorotoxin variants, conjugates, and compositions.

In one aspect, the invention provides a modified chlorotoxin peptide having a single lysine residue (Lys 27). In one embodiment, the modified chlorotoxin peptide has Lys 15 and Lys 23 of native chlorotoxin substituted by an amino acid other than lysine. In one embodiment, the modified chlorotoxin peptide having the amino acid sequence set forth in SEQ ID NO: 2. In one embodiment, the modified chlorotoxin peptide has the amino acid sequence set forth in SEQ ID NO: 3. In one embodiment, the modified chlorotoxin peptide has the amino acid sequence set forth in SEQ ID NO: 4. In one embodiment, the modified chlorotoxin peptide has the amino acid sequence set forth in SEQ ID NO: 5. In one embodiment, the modified chlorotoxin peptide having the amino acid sequence set forth in SEQ ID NO: 6.

Compositions comprising a modified chlorotoxin peptide of the invention are also provided. In one embodiment, the composition comprises a pharmaceutically acceptable carrier.

In another aspect, the invention provides a method for treating a disease or condition treatable by administering chlorotoxin, comprising administering an effective amount of a modified chlorotoxin peptide of the invention to a subject in need thereof.

In a further aspect of the invention, a chlorotoxin conjugate comprising a modified chlorotoxin peptide of the invention is provided. In one embodiment, the chlorotoxin conjugate comprises a modified chlorotoxin peptide covalently coupled to one or more of a therapeutic, diagnostic, imaging, or targeting agent, or a moiety that increases the circulatory half-life of the modified chlorotoxin peptide. In one embodiment, the therapeutic, diagnostic, imaging, or targeting agent, or a moiety that increases the circulatory half-life of the modified chlorotoxin peptide is covalently coupled to the modified chlorotoxin peptide through the lysine residue. Suitable diagnostic or imaging agents include fluorescent labels (e.g., quantum dot or polymeric dot), radiolabels, and magnetic resonance imaging labels (e.g., a boron nanoparticle, a boron and carbon nanoparticle, a boron carbide nanoparticle, boron-containing polymer, a boron and carbon containing polymer, a boron carbide polymer, and any of these nanoparticles or polymers further comprising gadolinium). Suitable targeting agents include antibodies, polypeptides, polysaccharides, and nucleic acids. Suitable therapeutic agents include chemotherapeutic agents (e.g., methotrexate, docetaxel, cisplatin, and etoposide) and biological therapeutic agents (e.g., cDNA, siRNA, shRNA, and RNAi). Suitable moieties that increase the circulatory half-life of the modified chlorotoxin peptide include peg moieties, glycosyl moieties, and glycosylpeg moieties.

In other aspects, methods for using the chlorotoxin conjugates are provided.

In one embodiment, the invention provides a method for imaging a tissue imagable by chlorotoxin, comprising contacting a tissue imagable by chlorotoxin with a chlorotoxin conjugate of the invention to image a tissue imagable by chlorotoxin.

In one embodiment, the invention provides a method for detecting cancer detectable by chlorotoxin, comprising contacting a tissue imagable by modified chlorotoxin with a modified chlorotoxin conjugate of the invention to detect cancer detectable by chlorotoxin.

In one embodiment, the invention provides a method for detecting and removing cancer detectable by chlorotoxin, comprising contacting a tissue with a modified chlorotoxin conjugate of the invention to detect cancerous tissue, and removing the cancerous tissue detected by the modified chlorotoxin conjugate.

In one embodiment, the invention provides a method for treating cancer targeted by a modified chlorotoxin conjugate, comprising contacting a tissue that binds to modified chlorotoxin with a modified chlorotoxin conjugate of the invention to treat the cancer.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 3B, K15R_K23R CTX:Cy5.5). WT or ND2:SmoA1 tumor-bearing mice were injected with 50 μl of 40 μM modified bioconjugate through the tail vein. Biophotonic images were taken three days after the injection using the Xenogen Spectrum. The brains were then frozen in OCT, cut in 12 μm sections, and stained with H&E to determine tumor burden.

DETAILED DESCRIPTION OF THE INVENTION

Figure 1:
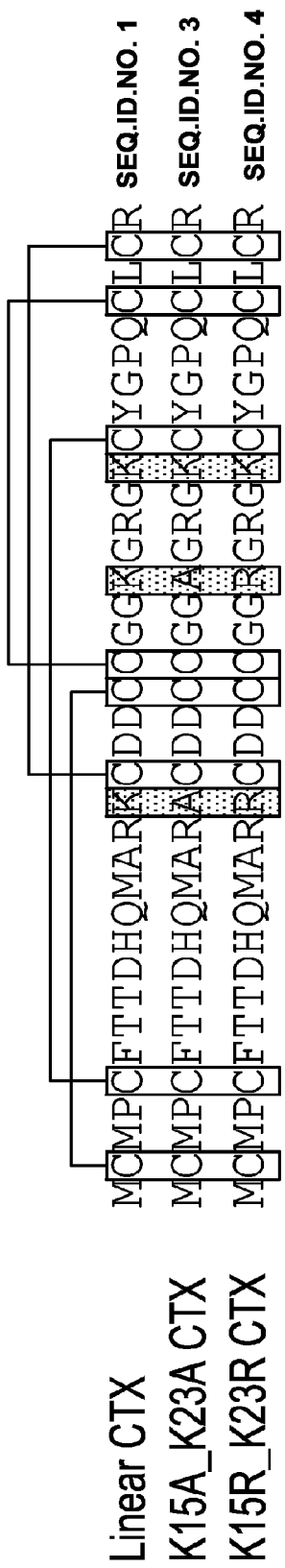
FIG. 1 compares the sequences of native chlorotoxin (Linear CTX) with representative modified chlorotoxin peptides of the invention (K15A_K23A CTX; K15R_K23R CTX). The sequences of native and substituted CTX with four disulfide bonds shown as yellow lines.

The present invention provides chlorotoxin variants, conjugates made from the chlorotoxin variants, compositions that include the chlorotoxin variants or conjugates, and methods for using the chlorotoxin variants, conjugates, and compositions.

In one aspect, the invention provides chlorotoxin variants. As used herein, the term "chlorotoxin variant" is used interchangeably with the term "modified chlorotoxin peptide" and refers to a non-native polypeptide possessing at least some of the useful activities of native chlorotoxin.

Chlorotoxin is a naturally occurring polypeptide comprising 36 amino acids and having the amino acid sequence set forth in SEQ ID NO: 1.

The term "modified chlorotoxin peptide" refers to a polypeptide having an amino acid sequence in which one or more of the amino acid residues of native chlorotoxin are substituted (i.e., replaced) with an amino acid residue other than that of the native chlorotoxin at that position. For example, residues 15 and 23 of native chlorotoxin are lysine residues; in certain embodiments of the invention, modified chlorotoxin peptides are provided having alanine or arginine residues at positions 15 and 23.

In one embodiment, the invention provides a modified chlorotoxin peptide having a single lysine residue (Lys 27). In this embodiment, the modified chlorotoxin peptide has Lys 15 and Lys 23 of native chlorotoxin substituted by an amino acid other than lysine to provide a modified chlorotoxin having a single lysine residue (Lys 27). In this embodiment, the modified chlorotoxin peptide has the amino acid sequence set forth in SEQ ID NO: 2, where Lys 15 and Lys 23 are substituted by an amino acid independently selected from the group consisting of naturally occurring and non-natural amino acids, amino acid analogs and amino acid mimetics.

Naturally occurring amino acids are the twenty L-amino acids commonly found in naturally occurring proteins (Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Non-natural amino acids include the D-amino acids. Amino acid analogs and amino acid mimetics function in a manner similar to the naturally occurring amino acids. Amino acid analogs refers to compounds that have the same basic chemical structure as a naturally occurring amino acid, by way of example only, an α-carbon that is bound to a hydrogen, a carboxyl group, an amino group, and an R group. Such analogs may have modified R groups (by way of example, norleucine) or may have modified peptide backbones, while still retaining the same basic chemical structure as a naturally occurring amino acid. Non-limiting examples of amino acid analogs include homoserine, norleucine, methionine sulfoxide, methionine methyl sulfonium.

In one embodiment, Lys 15 and/or Lys 23 are independently replaced with a basic amino acid (i.e., His, Arg), non-natural amino acid, amino acid analog, or amino acid mimetic.

In one embodiment, Lys 15 and/or Lys 23 are independently replaced with a nonpolar (hydrophobic) amino acid (i.e., Ala, Phe, Ile, Leu, Met, Pro, Val, Trp), related non-natural amino acid, amino acid analog, or amino acid mimetic.

In one embodiment, Lys 15 and/or Lys 23 are independently replaced with a polar (uncharged) amino acid (i.e., Cys, Gly, Asn, Gln, Ser, Thr, Tyr), non-natural amino acid, amino acid analog, or amino acid mimetic.

In one embodiment, Lys 15 and/or Lys 23 are independently replaced with an acidic amino acid (i.e., Glu, Asp), non-natural amino acid, amino acid analog, or amino acid mimetic.

In one embodiment, the modified chlorotoxin peptide has Lys 15 and Lys 23 substituted by alanine (K15A_K23A CTX). In this embodiment, the modified chlorotoxin peptide has the amino acid sequence set forth in SEQ ID NO: 3.

In one embodiment, the modified chlorotoxin peptide has Lys 15 and Lys 23 substituted by arginine (K15R_K23R CTX). In this embodiment, the modified chlorotoxin peptide has the amino acid sequence set forth in SEQ ID NO: 4.

In one embodiment, the modified chlorotoxin peptide has Lys 15 substituted by alanine and Lys 23 substituted by arginine (K15A_K23R CTX). In this embodiment, the modified chlorotoxin peptide has the amino acid sequence set forth in SEQ ID NO: 5.

In another embodiment, the modified chlorotoxin peptide has Lys 15 substituted by arginine and Lys 23 substituted by alanine (K15R_K23A CTX). In this embodiment, the modified chlorotoxin peptide has the amino acid sequence set forth in SEQ ID NO: 6.

In another aspect of the invention, compositions that include the modified chlorotoxin peptides are provided. The composition can include a pharmaceutically acceptable carrier or diluent for delivery of the modified chlorotoxin peptide. Suitable pharmaceutically acceptable carriers or diluents include saline or dextrose for injection.

Treatment Methods.

In a further aspect, the invention provides a method for treating a disease or condition treatable by administering chlorotoxin. In one embodiment, the method includes administering an effective amount of a modified chlorotoxin peptide of the invention to a subject in need thereof.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. Compositions containing such agents or compounds can be administered for prophylactic, enhancing, and/or therapeutic treatments. An appropriate "effective" amount in any individual case may be determined using techniques, such as a dose escalation study.

In one embodiment, the invention provides a method for treating a cancer that expresses chlorotoxin binding sites in a patient, comprising administering to a patient in need thereof an effective amount of a chlorotoxin variant of the invention.

In one embodiment, the invention provides a method for treating a cancer that expresses chlorotoxin binding sites, comprising administering to a patient in need thereof an effective amount of a pharmaceutical composition comprising a chlorotoxin variant of the invention and a pharmaceutically acceptable carrier.

In one embodiment, the invention provides a method for treating a tumor expressing chlorotoxin binding sites, comprising administering to a patient in need thereof an effective amount of a chlorotoxin variant of the invention.

In one embodiment, the invention provides a method for inhibiting invasive activity of cells that express chlorotoxin binding sites, comprising administering an effective amount of a chlorotoxin variant to cells that express chlorotoxin binding sites.

The methods of treatment of the invention are applicable to human and animal subjects in need of such treatment.

Virtually every type of malignant cancer expressing chlorotoxin binding sites can be treated by the chlorotoxin variants and conjugates of the invention. These malignant cancers include gliomas, astrocytomas medulloblastomas, choroids plexus carcinomas, ependymomas, meningioma, glioblastoma, ganglioma, pheochromocytoma, and metastatic brain tumors, other brain tumors, neuroblastoma, head and neck cancer, small cell lung cancer, breast cancer, intestinal cancer, pancreatic cancer, colon cancer, liver cancer, kidney cancer, skin cancer, sarcomas (over 30 types), osteosarcoma, rhabdomyosarcoma, Ewing's sarcoma, carcinomas, melanomas, ovarian cancer, cervical cancer, lymphoma, thyroid cancer, anal cancer, colo-rectal cancer, endometrial cancer, germ cell tumors, laryngeal cancer, multiple myeloma, prostate cancer, retinoblastoma, gastric cancer, testicular cancer, and Wilm's tumor.

Chlorotoxin Conjugates.

In another aspect, the invention provides conjugates of the modified chlorotoxin peptides of the invention. In one embodiment, the conjugates comprise a modified chlorotoxin peptide of the invention covalently coupled to a moiety that increases the circulatory half-life of the modified chlorotoxin peptide. In another embodiment, the conjugates comprise a modified chlorotoxin peptide of the invention covalently coupled to a therapeutic, diagnostic, imaging, or targeting agent. In certain embodiments, the therapeutic, diagnostic, imaging, or targeting agent, or moiety that increases the circulatory half-life of the modified chlorotoxin peptide is covalently coupled through the peptide's lysine residue.

Suitable moieties that increase the circulatory half-life of the modified chlorotoxin peptide include those known in the art for increasing the circulatory half-life of polypeptides (e.g., pegylation, glycosylation, glycopegylation). Representative moieties for pegylation include polyalkylene oxides (polyethylene oxides, polypropylene oxides, and copolymers of polyethylene oxides and polypropylene oxides). Representative moieties for glycosylation include oligosaccharides (e.g., carbohydrates including polysialic acids). In one embodiment, the conjugate is a pegylated chlorotoxin and comprises a modified chlorotoxin peptide covalently coupled to one or more polyalkylene oxides (e.g., polyethylene oxide). In one embodiment, the conjugate is a glycosylated chlorotoxin and comprises a modified chlorotoxin peptide covalently coupled to one or more oligosaccharides. In one embodiment, the conjugate is a glycopegylated chlorotoxin and comprises a modified chlorotoxin peptide covalently coupled to one or more glycopolyalkylene oxides (e.g., glycopolyethylene oxide).

Suitable therapeutic agents include cytotoxic agents. Representative therapeutic agents include chemotherapeutic agents such as methotrexate, docetaxel, cisplatin, and etoposide, among others; biological therapeutic agents such as nucleic acid molecules (e.g., DNA such as cDNA, and RNA such as siRNA, shRNA, RNAi) including transcription and translocation inhibitors, and signal transduction modulators.

Suitable diagnostic agents include agents that provide for the detection by fluorescence methods as well as methods other than fluorescence imaging. Other suitable diagnostic agents include radiolabels (e.g., radio isotopically labeled compounds) such as $^{125}$I, $^{14}$C, and $^{31}$P, among others; and magnetic resonance imaging agents.

Suitable targeting agents include antibodies, polypeptides, polysaccharides, and nucleic acids.

In another aspect of the invention, compositions that include the modified chlorotoxin peptide conjugates are provided. The composition can include a pharmaceutically acceptable carrier or diluent for delivery of the modified chlorotoxin peptide conjugate. Suitable pharmaceutically acceptable carriers or diluents include saline or dextrose for injection.

Imaging Methods.

In a further aspect of the invention, methods of using the modified chlorotoxin peptide conjugates are provided. In one embodiment, the invention provides a method for imaging a tissue imagable by chlorotoxin. In the method, a tissue imagable by chlorotoxin is contacted with a chlorotoxin conjugate.

In one embodiment, the imaging method is a fluorescence imaging method. Representative methods for making and using fluorescent chlorotoxin conjugates are described in U.S. Patent Application Publication No. 20080279780 A1, Fluorescent Chlorotoxin Conjugate and Method for Intra-Operative Visualization of Cancer, expressly incorporated herein by reference in its entirety.

The present invention provides a chlorotoxin conjugate detectable by fluorescence imaging that allows for intra-operative visualization of cancerous tissues, compositions that include the chlorotoxin conjugate, and methods for using the chlorotoxin conjugate.

In one aspect, the present invention provides a chlorotoxin conjugate detectable by fluorescence imaging that allows for intra-operative visualization of cancerous tissues.

The chlorotoxin is a targeting agent that directs the conjugate to a tissue of interest. In one embodiment, the chlorotoxin conjugate of the invention includes one or more fluorescent moieties (e.g., red or near infrared emitting fluorescent moieties) covalently coupled to the chlorotoxin.

As used herein, the term "red or near infrared emitting fluorescent moiety" refers to a fluorescent moiety having a fluorescence emission maximum greater than about 600 nm. Fluorescent chlorotoxin conjugates having shorter wavelength (e.g., from about 500 to about 600 nm) emitting fluorescent moieties are useful in histochemical imaging. These conjugates may be useful less for in vivo imaging in humans and animals where longer wavelength (e.g., greater than about 600 nm) emitting fluorescent moieties are preferred.

In certain embodiments of the chlorotoxin conjugate, the fluorescent moieties are derived from fluorescent compounds characterized by emission wavelength maxima greater than about 600 nm to avoid autofluorescence, emission that travels through millimeters to one centimeter of tissue/blood/fluids, emission that is not absorbed by hemoglobin, other blood components, or proteins in human or animal tissue.

The fluorescent moiety is covalently coupled to the chlorotoxin to allow for the visualization of the conjugate by fluorescence imaging. The fluorescent moiety is derived from a fluorescent compound. Suitable fluorescent compounds are those that can be covalently coupled to a chlorotoxin without substantially adversely affecting the targeting and binding function of the chlorotoxin conjugate. Similarly, suitable fluorescent compounds retain their fluorescent properties after conjugation to the chlorotoxin.

In one embodiment, the fluorescent moiety is a cyanine moiety. Cyanine compounds are characterized by their relative high extinction coefficients and favorable fluorescence quantum yields. The fluorescence emission wavelength maximum for a cyanine compound varies as a function of the cyanine structure. Depending on the particular cyanine compound, the fluorescence emission wavelength maxima can vary from the green (about 490 nm) to the near infrared (about 740 nm). In the practice of the methods of the invention, cyanine compounds having fluorescence emission maxima in the far red (about 650 nm) to the near infrared (about 750 nm) are preferred. At these emission wavelengths, background fluorescence from the local environment is minimal and tissues of interest are relatively transparent. Because of the relative transparency of the tissues of interest at these wavelengths, excitation and fluorescence emission visualization is maximized and relatively greater amounts of tissue targeted by the conjugate of the invention can be observed compared to other conjugates utilizing fluorescent compounds having emission at shorter wavelengths (less than 600 nm).

Suitable cyanines include the CYDYE fluors commercially available from GE Healthcare under the designation Cy2 (506 nm); Cy2 (506 nm); Cy3 (570 nm); Cy3B (572 nm); Cy3.5 (596 nm); Cy5 (670 nm); Cy5.5 (675 nm); and Cy7 (694 nm) (emission maxima in parentheses). In one embodiment, the cyanine compound is Cy5.5.

In one embodiment, the fluorescent moiety is a sulfonated xanthene moiety. Sulfonated xanthene compounds suitable for use in the practice of the invention are described in U.S. Pat. No. 6,130,101, expressly incorporated herein by reference in its entirety, and commercially available under the designation ALEXA FLUOR from Molecular Probes, Inc., Eugene, Oreg. ALEXA FLUOR is the designation for a family of fluorophores that are characterized by their relative high extinction coefficients and favorable fluorescence quantum yields. The fluorescence emission wavelength maximum for a sulfonated xanthene compound varies as a function of the compound's structure. Depending on the particular sulfonated xanthene compound, the fluorescence emission wavelength maxima can vary from the green (about 450 nm) to the near infrared (about 780 nm). In the practice of the methods of the invention, ALEXA FLUOR compounds having fluorescence emission maxima in the far red (about 650 nm) to the near infrared (about 750 nm) are preferred.

Suitable sulfonated xanthene compounds include ALEXA FLUORS, such as ALEXA FLUOR 350 (442 nm), ALEXA FLUOR 405 (421 nm), ALEXA FLUOR 488 (539 nm), ALEXA FLUOR 500 (525 nm), ALEXA FLUOR 514 (540 nm), ALEXA FLUOR 532 (554 nm), ALEXA FLUOR 546 (575 nm), ALEXA FLUOR 555 (565 nm), ALEXA FLUOR 568 (603 nm), ALEXA FLUOR 594 (617 nm), ALEXA FLUOR 610 (628 nm), ALEXA FLUOR 633 (647 nm), ALEXA FLUOR 635 (645 nm), ALEXA FLUOR 647 (668 nm), ALEXA FLUOR 660 (690 nm), ALEXA FLUOR 680 (702 nm), ALEXA FLUOR 700 (719 nm), and ALEXA FLUOR 750 (779 nm) (emission maxima in parentheses). In one embodiment, the sulfonated xanthene is ALEXA FLUOR 680. Representative sulfonated xanthene-chlorotoxin conjugates can be prepared in manner analogous to that described in *The Handbook—A Guide to Fluorescent Probes and Labeling Technologies*, Richard P. Haugland (Molecular Probes, Inc., a subsidiary of Invitrogen Corp.).

Other suitable NIR fluorophores useful in the invention include DyLight-680, DyLight-750, VivoTag-750, DyLight-800, IRDye-800, VivoTag-680, and indocyanine green.

The modified chlorotoxin peptides of the invention can also be coupled to quantum dots and polymer dots.

Suitable fluorescent compounds include a functional group that renders the compound chemically reactive toward the chlorotoxin. Suitable functional groups include the N-hydroxysuccinimide (NHS) group for covalent coupling to amine groups, the maleimide group for covalent coupling to thiol groups, and the hydrazide group for covalent coupling to aldehyde groups. Preferably, the fluorescent compound useful in preparing the conjugate of the invention includes a single reactive functional group (e.g., mono-NHS ester). It will be appreciated that other conjugating chemistries are suitable for making the chlorotoxin conjugate of the present invention.

Suitable conjugates of the invention include from about 1 to about 3 fluorescent moieties/chlorotoxin. In one embodiment, the conjugate includes about 1 fluorescent moiety.

In another aspect of the invention, compositions that include the chlorotoxin conjugate are provided. The composition is suitable for administration to a human and animal subjects and includes pharmaceutically acceptable carrier. The composition includes a pharmacologically effective amount of a modified chlorotoxin conjugate. An effective amount can be routinely determined by established procedures. An effective amount is an amount sufficient to occupy chlorotoxin binding sites in cancer cells, but low enough to minimize non-specific binding to non-neoplastic tissues. An effective amount optimizes signal-to-noise ratio for intra-operative imaging.

The invention provides methods for detecting a tissue using the chlorotoxin conjugates. The chlorotoxin conjugates of the invention target and are bound by chlorotoxin binding sites. It will be appreciated that chlorotoxin binding sites may take two forms: sites that bind chlorotoxin and sites that bind the chlorotoxin conjugates of the invention. It will be appreciated that chlorotoxin binding sites may be distinct from chlorotoxin conjugate binding sites.

In one embodiment, a method for differentiating foci of cancers that express chlorotoxin binding sites from non-neoplastic tissue is provided. The method includes the steps of:

(a) contacting a tissue of interest with a chlorotoxin conjugate having affinity and specificity for cells that express chlorotoxin binding sites, wherein the chlorotoxin conjugate comprises one or more red or near infrared emitting fluorescent moieties covalently coupled to a chlorotoxin; and (b) measuring the level of binding of the chlorotoxin conjugate, wherein an elevated level of binding, relative to normal tissue, is indicative that the tissue is neoplastic.

In one embodiment, a method for detecting cancers that express chlorotoxin binding sites is provided. The method includes the steps of:

(a) contacting a tissue of interest with a chlorotoxin conjugate having affinity and specificity for cells that express chlorotoxin binding sites, wherein the chlorotoxin conjugate comprises one or more red or near infrared emitting fluorescent moieties covalently coupled to a chlorotoxin; and (b) measuring the level of binding of the chlorotoxin conjugate, wherein an elevated level of binding, relative to normal tissue, is indicative that the tissue is neoplastic.

In one embodiment, a method for determining the location of cancer cells that express chlorotoxin binding sites in a patient intra-operatively is provided. The method includes the steps of:

(a) administering a pharmaceutical composition to a patient, wherein the pharmaceutical composition comprises a pharmaceutically acceptable carrier and an amount of a chlorotoxin conjugate sufficient to image cancer cells that express chlorotoxin binding sites in vivo, wherein the chlorotoxin conjugate comprises one or more red or near infrared emitting fluorescent moieties covalently coupled to a chlorotoxin;

(b) measuring the level of binding of the chlorotoxin conjugate by fluorescence imaging to determine the location of cancer cells that express chlorotoxin binding sites, wherein an elevated level of binding, relative to normal tissue, is indicative of the presence of cancer cells that express chlorotoxin binding sites; and (c) surgically removing from the patient at least some cells that express chlorotoxin binding sites located by fluorescence imaging.

The imaging methods of the invention for detection of cancer foci is applicable to mouse and other animal models of cancer as well as to veterinary practice.

The fluorescent chlorotoxin conjugate of the invention may include other useful agents. Other useful agents include diagnostic agents and therapeutic agents.

In another embodiment, the imaging method is a magnetic resonance imaging method. Representative methods for making and using chlorotoxin conjugates in magnetic resonance imaging are described in U.S. Patent Application Publication No. 200701254965 A1, Chlorotoxin-Labeled Nanoparticle Compositions and Methods for Targeting Primary Brain Tumors, expressly incorporated herein by reference in its entirety.

The present invention provides chlorotoxin-labeled nanoparticles capable of targeting primary brain tumors, compositions that include the nanoparticles, methods of imaging tissues using the nanoparticles, and methods for treating cells expressing chlorotoxin binding sites using the nanoparticles.

In one aspect, the invention provides a chlorotoxin-labeled particle comprising:

(a) a core having a surface, the core comprising a material having magnetic resonance imaging activity;

(b) a modified chlorotoxin peptide; and (c) a linker covalently coupling the modified chlorotoxin peptide to the surface.

The core includes a material having magnetic resonance imaging activity. Suitable materials having magnetic resonance imaging activity include metal oxides, such as ferrous oxide, ferric oxide, silicon oxide, polycrystalline silicon oxide, aluminum oxide, germanium oxide, zinc selenide, tin dioxide, titanium dioxide, indium tin oxide, and gadolinium oxide. Mixtures of one or more metal oxide can be used.

In addition to magnetic materials, the core can include non-magnetic materials, such as silicon nitride, stainless steel, titanium, boron, boron carbide, boron and carbon mixtures, and nickel titanium. Mixtures of one or more non-magnetic materials can also be used.

The particles of the invention include from about 1 to about 100 modified chlorotoxins/particle. In one embodiment, the particles include from about 10 to about 50 modified chlorotoxins/particle. In one embodiment, the particles include about 10 modified chlorotoxins/particle. In one embodiment, the particles include about 50 to about 100 modified chlorotoxins/particle.

As noted above, the magnetic nanoparticle of the invention includes a chlorotoxin that serves as a targeting moiety that is effective to direct the nanoparticle to cells expressing chlorotoxin binding sites where the nanoparticle is bound. Primary brain tumor cells (e.g., neuroectodermal-derived tumor cells and glioma cells) include chlorotoxin binding sites.

The chlorotoxin-labeled nanoparticles can further include other useful agents. Other useful agents include diagnostic agents.

Suitable diagnostic agents include agents that provide for the detection of the nanoparticle by methods other than magnetic resonance imaging. Suitable diagnostic agents include light-emitting compounds (e.g., fluorophores, phosphors, and luminophors). Suitable fluorophores include those noted above.

In one embodiment, the chlorotoxin-labeled particle further comprises a fluorescent moiety. The particles of the invention include from about 1 to about 10 fluorescent moieties/particle. In one embodiment, the particles include from about 1 to about 2 fluorescent moieties/particle.

In one embodiment, the fluorescent moiety is selected from red and near infrared emitting fluorescent moieties (i.e., fluorescent moieties having emission maxima greater than about 600 nm). In one embodiment, the fluorescent moiety is a cyanine moiety. In one embodiment, the fluorescent moiety is a Cy5.5 moiety.

Other suitable diagnostic agents include radiolabels (e.g., radio isotopically labeled compounds) such as $^{125}$I, $^{14}$C, and $^{31}$P, among others.

In another aspect of the invention, compositions that include the particles of the invention are provided. In one embodiment, the composition includes a nanoparticle suitable for administration to a human or an animal subject. The composition can include an acceptable carrier. In one embodiment, the composition is a pharmaceutically acceptable composition and includes a pharmaceutically acceptable carrier. As used herein the term "carrier" refers to a diluent (e.g., saline) to facilitate the delivery of the particles.

In other aspects, the invention provides methods for using nanoparticles.

In one embodiment, the invention provides a method for differentiating neuroectodermal-derived tumor cells from non-neoplastic brain tissue. In the method, neuroectodermal-derived tumor cells are differentiated from non-neoplastic brain tissue by:

(a) contacting a tissue of interest with a chlorotoxin-labeled nanoparticle having affinity and specificity for neuroectodermal-derived tumor cells; and (b) measuring the level of binding of the chlorotoxin-labeled nanoparticle, wherein an elevated level of binding, relative to normal tissue, is indicative that the tissue is neoplastic.

In one embodiment, the invention provides a method for detecting neuroectodermal-derived tumor cells. In the method, neuroectodermal-derived tumor cells are detected by:

(a) contacting a tissue of interest with a chlorotoxin-labeled nanoparticle having affinity and specificity for neuroectodermal-derived tumor cells; and (b) measuring the level of binding of the chlorotoxin-labeled nanoparticle, wherein an elevated level of binding, relative to normal tissue, is indicative that the tissue is neoplastic.

The above methods are useful in differentiating and detecting glioma cells.

In the methods above, measuring the level of binding of the chlorotoxin-labeled nanoparticle comprises magnetic resonance imaging.

In certain embodiments of the methods above, the chlorotoxin-labeled nanoparticle further comprises a fluorescent moiety. In these embodiments, measuring the level of binding of the chlorotoxin-labeled nanoparticle can include fluorescence imaging.

In one embodiment, the invention provides a method for determining the location of glioma cells in a patient pre-operatively, intra-operatively, and post-operatively. The methods includes the steps of:

(a) administering a pharmaceutical composition to a patient, wherein the pharmaceutical composition comprises a pharmaceutically acceptable carrier and an amount of a fluorophore/chlorotoxin-labeled nanoparticle sufficient to image glioma cells in vivo;

(b) measuring the level of binding of the fluorophore/chlorotoxin-labeled nanoparticle by magnetic resonance imaging pre-operatively to determine the location of glioma cells, wherein an elevated level of binding, relative to normal tissue, is indicative of the presence of glioma cells;

(c) surgically removing from the patient at least some glioma cells located by magnetic resonance imaging;

(d) measuring the level of binding of the fluorophore/chlorotoxin-labeled nanoparticle by fluorescence imaging intra-operatively to determine the location of residual glioma cells, wherein an elevated level of binding, relative to normal tissue, is indicative of the presence of residual glioma cells;

(e) surgically removing from the patient at least some residual glioma cells located by fluorescence imaging; and (f) measuring the level of binding of the fluorophore/chlorotoxin-labeled nanoparticle by magnetic resonance imaging post-operatively to determine the location of glioma cells, wherein an elevated level of binding, relative to normal tissue, is indicative of the presence of glioma cells.

In the method, an amount of a fluorophore/chlorotoxin-labeled nanoparticle sufficient to image glioma cells in vivo is an amount from about 1-20 mg Fe/kg body weight ("Fe" refers to iron present in particle core).

In the above method, steps (d) and (e) may be repeated.

The above method includes pre-operative, intra-operative, and post-operative imaging. It will be appreciated that variations of the above method are within the scope of the invention. Other variations of the method include, for example, (1) pre-operative imaging only; (2) intra-operative imaging only; (3) post-operative imaging only; (4) pre-operative and intra-operative imaging only; (5) pre-operative and post-operative imaging only; and (6) intra-operative and post-operative imaging only.

The invention provides methods for treating a tissue using the nanoparticles.

In one embodiment, the invention provides a method for treating a glioma in a patient, comprising administering to a patient in need thereof an effective amount of a pharmaceutical composition comprising a chlorotoxin-labeled nanoparticle and a pharmaceutically acceptable carrier.

In one embodiment, the invention provides a method for treating a neuroectodermal tumor, comprising administering to a patient in need thereof an effective amount of a pharmaceutical composition comprising a chlorotoxin-labeled nanoparticle and a pharmaceutically acceptable carrier.

In one embodiment, the invention provides a method for inhibiting invasive activity of neoplastic cells, comprising administering to neoplastic cells an effective amount of a pharmaceutical composition comprising a chlorotoxin-labeled nanoparticle and a pharmaceutically acceptable carrier.

The following describes three representative modified chlorotoxin peptides of the invention and their properties, conjugates of the peptides and their properties, and use of the conjugates in imaging.

Preparation of Modified Chlorotoxin Peptides.

Two representative modified chlorotoxin (CTX) peptides of the invention (alanine substituted chlorotoxin, K15A_K23A-CTX; arginine substituted chlorotoxin, K15R_K23R-CTX) sequences are shown in FIG. 1. The peptides were synthesized using Boc (tert-butoxycarbonyl)/HBTU [2-(1H-benzotriazol-1-yl)-1,1,3,3-tetramethyluronium hexafluorophosphate] in situ neutralization chemistry. A buffer solution of 0.1 M Tris-HCl, 0.2 M NaCl, 5 mM reduced glutathione/0.5 mM oxidized glutathione with a pH 7.8 was used both to oxidize the substituted peptides and to cyclize and oxidize CTX at room temperature overnight. RP-HPLC was used to purify the peptides, and the purity and the molecular masses of the two CTX analogues K15A_K23A-CTX and K15R_K23R-CTX were confirmed by analytical RP-HPLC and ES-MS.

NMR Assignment.

Figure 2:
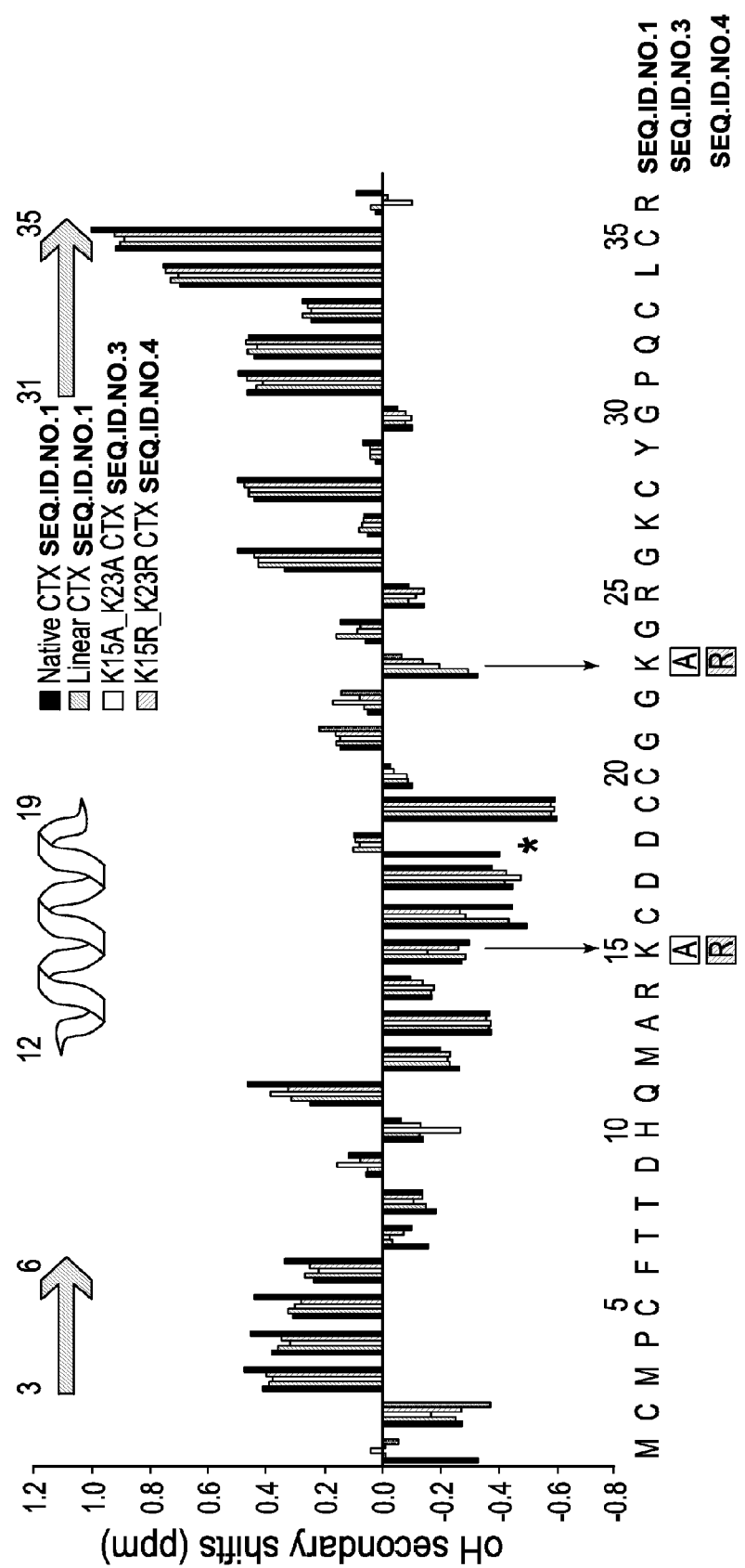
FIG. 2 is a comparison of the secondary αH chemical shifts of representative modified chlorotoxin peptides of the invention and native chlorotoxin. The secondary αH shifts were calculated by subtracting the random coil shifts from the experimental αH shifts (D. S. Wishart, et al., $^1$H, $^{13}$C and $^{15}$N Chemical Shift Referencing in Biomolecular NMR," *Journal of Biomolecular NMR* 6, 135-140, 1995). A bar graph for native CTX (dark blue), linear CTX (blue), K15A_K23A CTX (red), and K15R_K23R CTX (orange). Two β-strands are shown as blue arrow, α-helix is shown in red. The substituted residues and residue D18 are shown with a green asterisk.
Figure 3B:
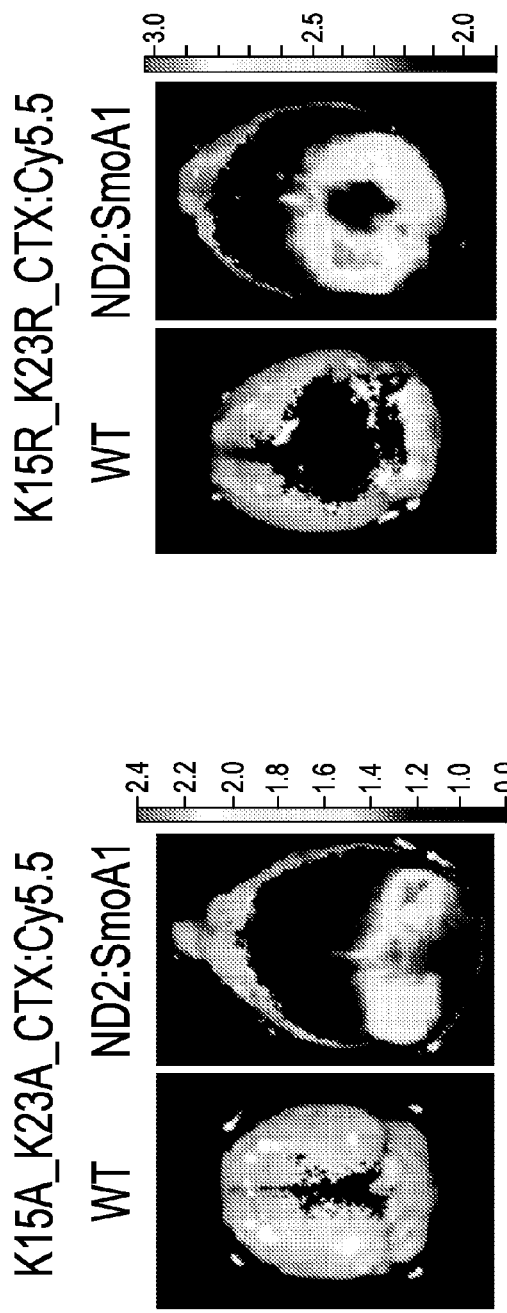
FIGS. 3A and 3B illustrate functional imaging with representative modified CTX:Cy5.5 bioconjugates of the invention (FIG. 3A, K15A_K23A CTX:Cy5.5.
Figure 3B:
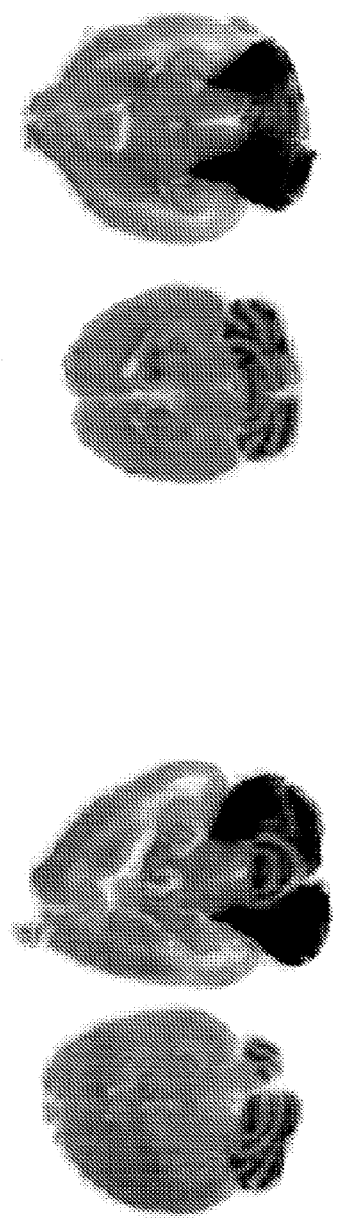
Figure 3A:
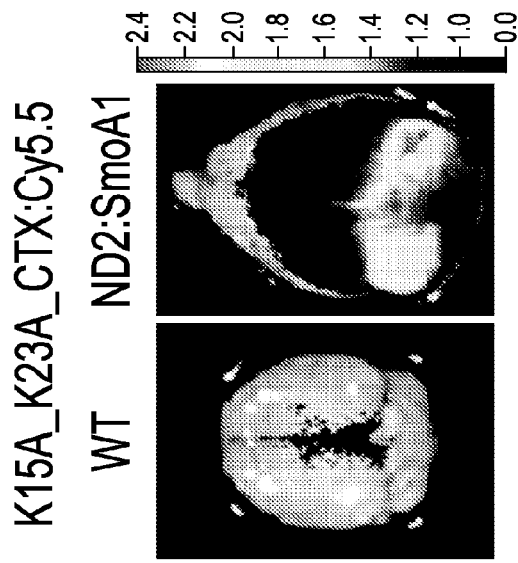
Figure 3A:
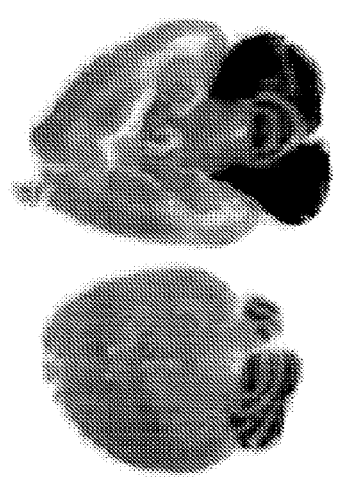

The peptides were dissolved in 90% $H_2O$ and 10% $D_2O$, and one-dimensional and two-dimensional TOCSY and NOESY spectra were recorded at 600 MHz at 298° K. The NMR spectra were assigned using well established techniques (K. Wuthrich, "NMR of Proteins and Nucleic Acids", Wiley-Interscience, New York, 1986). Chemical shifts in the amide region are well dispersed, confirming that the peptides are correctly folded, and the fingerprint region in the NOESY spectrum of each peptide shows a complete cycle of αH—NH sequential connectivities with the exception of the two proline residues (Pro4 and Pro31). However, as expected, NOEs were observed from the δ protons of the proline residues and their preceding residues. A comparison of secondary αH chemical shifts of native CTX and the synthesized analogues are shown in FIG. 2.

Characterization of Substituted CTX Bioconjugates.

The native and modified peptides were conjugated to Cy5.5 and purified as described below in the Examples. Resulting bioconjugates were analyzed by HPLC and mass spectrometry. As predicted, the Ala and Arg substitutions resulted solely in mono-labeled CTX:Cy5.5 bioconjugates.

Functional Assessment of Substituted CTX:

Cy5.5. The potential benefits of substitution depend on whether the functional targeting activity of the peptides is comparable to native CTX bioconjugates. The capacity of each peptide to target Cy5.5 signal to medulloblastoma cells preferentially, over normal brain was assayed by biophotonic imaging. In each case, 50 μL of 40 μM bioconjugate was injected into the tail vein of mice that showed clinical signs consistent with advanced brain tumors. After three days the mice were sacrificed and their brains were imaged using the Caliper/Xenogen Spectrum biophotonic imaging system. All of the modified peptide conjugates preferentially illuminated medulloblastoma cancer tissue compared with normal brain (FIGS. 3A and 3B). In all cases, signal in the tumor was compared with signal in cerebellum of injected control animals that did not have medulloblastoma. The signal in tumor compared with normal was 1.96+/−0.47 for native CTX:Cy5.5 (n=10); 3.3+/−1.8 for Ala substituted (n=8) and 2.6+/−0.85 for Arg substituted (n=5). Statistically, all of the modified peptide bioconjugates were indistinguishable from native CTX:Cy5.5 indicating that lysine substitutions did not interfere with CTX binding to its target.

Advantages of the Invention.

When advancing a new therapeutic toward human clinical trials, consideration is given not only to efficacy, pharmacokinetics, pharmacodynamics and toxicity, but also practical issues that could compromise regulatory approval or increase manufacturing costs. Tumor Paint, a bioconjugate that safely and effectively illuminated solid tumors in mouse models, posed a manufacturing challenge related to the fact that the bioconjugate was actually a mixture of mono-, di- and tri-labeled CTX. The present invention provides three new representative chemical entities that are functionally equivalent to CTX for targeting NIRF molecules to cancer yet conjugate to only a single NIRF molecule.

CTX conjugation sites in CTX:Cy5.5 were mapped using arginase cleavage coupled with proteomic analyses and showed that typically >80% of product was mono-labeled at Lys 27 and lesser amounts were also conjugated at Lys 15 or Lys 23. In an analysis of CTX conjugated to four other NIRF dyes, similar patterns of predominantly mono-labeled peptide with smaller amounts of di- and tri-labeled peptide were observed, with the exception of Dylight 750, a NIRF dye that creates only mono-labeled species. The fact that Dylight 750 binds in a monomeric fashion to unmodified CTX suggests that access to the other two lysines is limited.

None of the lysine residues in CTX seem to be involved in the active binding of CTX to its target on cancer cells. This conclusion is based on the observations that target binding is preserved despite substitution of Lys 15 or Lys 23 with Ala or Arg and that addition of bulky Cy5.5 or other NIRF dyes to Lys 27 does not preclude binding to the active site.

Experimental Procedures

Solid Phase Peptide Synthesis.

Manual solid-phase peptide synthesis (SPPS) was used to synthesize the peptides with standard protecting groups (e.g. Asn(Xan), Asp(OcHex), Arg(TOS), Cys(MeBzl), Lys(ClZ), Ser(Bzl), Thr(Bzl) and Tyr(BrZ)). The Ala and Arg substituted linear CTX were assembled onto PAM-Arg resin without a thioester linker. Cleavage of the peptides from the resin was achieved by using hydrogen fluoride (HF) with p-cresol and p-thiocresol as scavengers (9:0.8:0.2 (vol/vol) HF:p-cresol:p-thiocresol) at −5 to 0° C. for 1.5 h. Reversed Phase-High Performance Liquid Chromatography (RP-HPLC) with a $C_{18}$ column was used to purify the peptides using a gradient of 0-80% Solution B (Solution A: $H_2O$/0.05% trifluoroacetic acid; Solution B: 90% $CH_3CN$/10% $H_2O$/0.045% trifluoroacetic acid) by monitoring the absorbance at 215 nm. Electro Spray Mass Spectroscopy (ES-MS) confirmed the purity and molecular mass of the synthesized peptides.

Folding.

The Ala and Arg substituted analogues were oxidized in an aqueous buffer solution consisting of 0.1 M Tris-HCl, 0.2 M NaCl, 5 mM reduced glutathione/0.5 mM oxidized glutathione with a pH 7.8 at room temperature overnight. RP-HPLC was used to purify the peptides and the purity and the molecular weights were confirmed by analytical RP-HPLC and ES-MS.

NMR Spectroscopy.

600 MHz $^1H$ NMR spectroscopy was used to monitor the three-dimensional structures of the peptide analogues. The peptide samples were dissolved in 90% $H_2O$ and 10% $D_2O$ (v/v). $D_2O$ (99.99%) was obtained from Cambridge Isotope Laboratories, Woburn, Mass. Two-dimensional NMR experiments included Total Correlation Spectroscopy (TOCSY) and Nuclear Overhauser Effect Spectroscopy (NOESY) spectra were recorded at 298° K.

Serum Stability Assay.

Serum stability assay was carried out in 100% human male serum (Sigma) using a 20 μM final peptide concentration. The serum was centrifuged at 14000 g for 10 min to remove the lipid component and the supernatant was incubated at 37° C. for 15 min prior to the assay. Each peptide was incubated in serum at 37° C. and 40 μL triplicate aliquots were taken out at 0, 1, 3, 6, 10, 16 and 24 h. Each serum aliquot was quenched with 40 μL of 6 M urea and incubated for 10 min at 4° C. Then, each serum aliquot was quenched with 40 μL of 20% trichloroacetic acid and incubated for another 10 min at 4° C. to precipitate serum proteins. The samples were centrifuged at 14000 g for 10 min, and 100 μL of the supernatant was analyzed on RP-HPLC using a linear gradient of solvent B (0.3 mL/min flow rate). The control samples contained equivalent amount of peptides in phosphate-buffered saline subjected to the same treatment procedure. The percentage recovery of peptides was detected by integration at 215 nm.

Animal Models.

All animals were handled in strict accordance with the National Institutes of Health Guide for the Care and Use of Laboratory Animals. All animal studies were conducted in accordance with Fred Hutchinson Cancer Research Center's Institute of Animal Care and Use Committee approved protocols. An autochthonous mouse model of medulloblastoma, ND2:SmoA1 (A. R. Hallahan, et al., "The SmoA1 Mouse Model Reveals That Notch Signaling is Critical for the Growth and Survival of Sonic Hedgehog-Induced Medulloblastomas," *Cancer Research* 64:7794-7800, 2004. B. A. Hatton, et al. "The Smo/Smo Model: Hedgehog-Induced Medulloblastoma With 90% Incidence and Leptomeningeal Spread," *Cancer Research* 68:1768-1776, 2008), on a C57bl/6 background was used to evaluate the specificity of cyclized CTX:Cy5.5, K15A_K23A CTX:Cy5.5, and K15R_K23R CTX:Cy5.5. Hemizygous or homozygous (referred as ND2:SmoA1) mice with symptomatic medulloblastoma were selected for enrollment in these studies. Symptoms were detected using an open field cage evaluation. Symptoms include head tilt, hunched posture, ataxia, protruding skull, and weight loss.

Ex Vivo Imaging.

ND2:SmoA1 animals exhibiting symptoms of medulloblastoma were injected with 50 μL of 40 μM K15A_K23A CTX:Cy5.5 or K15R_K23R CTX:Cy5.5 through the tail vein. Mice were euthanized using $CO_2$ inhalation three days after injection and ex vivo biophotonic images of their brain obtained using the Xenogen Spectrum Imaging System (Caliper). The brains were then frozen in Tissue-Tek Optimal Cutting Temperature (OCT) Compound (Sakura), sliced in 12 μm sections and Hemotoxylin and Eosin (H&E) stained according to standard procedures.

While the preferred embodiment of the invention has been illustrated and described, it will be appreciated that various changes can be made therein without departing from the spirit and scope of the invention.

The invention claimed is:

1. A chlorotoxin conjugate comprising a modified chlorotoxin polypeptide covalently conjugated to a fluorescent moiety comprising indocyanine green, the modified chlorotoxin polypeptide comprising an amino acid sequence corresponding to that of native chlorotoxin (SEQ ID NO: 1) in which lysine residue K15, lysine residue K23, or a combination thereof are substituted with an amino acid other than lysine, and wherein the chlorotoxin conjugate binds to chlorotoxin binding sites expressed by cancer cells.

2. The chlorotoxin conjugate of claim 1, wherein the lysine residue K15 and the lysine residue K23 of the modified chlorotoxin polypeptide are substituted by an amino acid other than lysine.

3. The chlorotoxin conjugate of claim 2, wherein the amino acid other than lysine is a natural amino acid or a non-natural amino acid.

4. The chlorotoxin conjugate of claim 2, wherein the amino acid other than lysine is alanine or arginine.

5. The chlorotoxin conjugate of claim 1, wherein the modified chlorotoxin polypeptide comprises a lysine residue at position 27.

6. The chlorotoxin conjugate of claim 1, wherein the modified chlorotoxin polypeptide comprises a lysine residue at position 15.

7. The chlorotoxin conjugate of claim 1, wherein the modified chlorotoxin polypeptide comprises a lysine residue at position 23.

8. The chlorotoxin conjugate of claim 1, wherein the modified chlorotoxin polypeptide is conjugated to a therapeutic, diagnostic, imaging, or targeting agent, or a moiety that increases the circulatory half-life of the modified chlorotoxin polypeptide.

9. The chlorotoxin conjugate of claim 8, wherein the therapeutic agent is a chemotherapeutic agent or a biological therapeutic agent.

10. The chlorotoxin conjugate of claim 8, wherein the therapeutic agent is methotrexate, docetaxel, cisplatin, etoposide, cDNA, siRNA, shRNA, or RNAi.

11. The chlorotoxin conjugate of claim 8, wherein the diagnostic or imaging agent is a fluorescent label, a radiolabel, or a magnetic resonance imaging label.

12. The chlorotoxin conjugate of claim 1, wherein the modified chlorotoxin polypeptide comprises the amino acid sequence of SEQ ID NO: 1 in which the lysine residue K15, the lysine residue K23, or a combination thereof are substituted with a basic, non-polar, polar or acidic amino acid, or a non-natural amino acid, amino acid analog, or amino acid mimetic thereof.

13. The chlorotoxin conjugate of claim 1, wherein the modified chlorotoxin polypeptide comprises the amino acid sequence of SEQ ID NO: 1 in which the lysine residue K15 and the lysine residue K23 are substituted by alanine or arginine.

14. The chlorotoxin conjugate of claim 1, wherein the modified chlorotoxin polypeptide comprises the amino acid sequence of SEQ ID NO: 1 in which the lysine residue K15 is substituted by alanine and the lysine residue K23 is substituted by arginine.

15. The chlorotoxin conjugate of claim 1, wherein the modified chlorotoxin polypeptide comprises the amino acid sequence of SEQ ID NO: 1 in which the lysine residue K15 is substituted by arginine and the lysine residue K23 is substituted by alanine.

16. A tissue or cell that has been removed from a subject, the tissue or cell comprising a cancerous tissue or cancerous cell bound to the chlorotoxin conjugate of claim 1.

17. The chlorotoxin conjugate of claim 1, wherein the modified chlorotoxin polypeptide has an amino acid sequence selected from the group consisting of:
SEQ ID NO: 2;
SEQ ID NO: 3;
SEQ ID NO: 4;
SEQ ID NO: 5; and
SEQ ID NO: 6.

18. The chlorotoxin conjugate of claim 6, wherein the indocyanine green is conjugated to the lysine residue at position 15.

19. The chlorotoxin conjugate of claim 7, wherein the indocyanine green is conjugated to the lysine residue at position 23.

20. The chlorotoxin conjugate of claim 5, wherein the indocyanine green is conjugated to the lysine residue at position 27.

21. A pharmaceutical composition comprising a pharmaceutically acceptable carrier and a chlorotoxin conjugate comprising a modified chlorotoxin polypeptide covalently conjugated to a fluorescent moiety comprising indocyanine green, the modified chlorotoxin polypeptide comprising an amino acid sequence corresponding to that of native chlorotoxin (SEQ ID NO: 1) in which lysine residue K15, lysine residue K23, or a combination thereof are substituted with an amino acid other than lysine, and wherein the chlorotoxin conjugate binds to chlorotoxin binding sites expressed by cancer cells.

22. The pharmaceutical composition of claim 21, wherein the modified chlorotoxin polypeptide comprises a lysine residue at position 27.

23. The pharmaceutical composition of claim 21, wherein the modified chlorotoxin polypeptide has an amino acid sequence selected from the group consisting of:
SEQ ID NO: 2;
SEQ ID NO: 3;
SEQ ID NO: 4;
SEQ ID NO: 5; and
SEQ ID NO: 6.

* * * * *

SEQUENCE LISTING

```
<160> NUMBER OF SEQ ID NOS: 6

<210> SEQ ID NO 1
<211> LENGTH: 36
<212> TYPE: PRT
<213> ORGANISM: Homo sapiens

<400> SEQUENCE: 1

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 2
<211> LENGTH: 36
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: Xaa can be any amino acid
<220> FEATURE:
<221> NAME/KEY: MISC_FEATURE
<222> LOCATION: (23)..(23)
<223> OTHER INFORMATION: Xaa can be any amino acid

<400> SEQUENCE: 2

Met Cys Met Pro Cys Phe Thr Thr Asp His Gln Met Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 3
<211> LENGTH: 36
<212> TYPE: PRT
<213> ORGANISM: Homo sapiens

<400> SEQUENCE: 3

Met Cys Met Pro Cys Phe Thr Thr Asp His Gln Met Ala Arg Ala Cys
1               5                   10                  15
```

```
Asp Asp Cys Cys Gly Gly Ala Gly Arg Gly Lys Cys Tyr Gly Pro Gln
            20                  25                  30

Cys Leu Cys Arg
        35

<210> SEQ ID NO 4
<211> LENGTH: 36
<212> TYPE: PRT
<213> ORGANISM: Homo sapiens

<400> SEQUENCE: 4

Met Cys Met Pro Cys Phe Thr Thr Asp His Gln Met Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 5
<211> LENGTH: 36
<212> TYPE: PRT
<213> ORGANISM: Homo sapiens

<400> SEQUENCE: 5

Met Cys Met Pro Cys Phe Thr Thr Asp His Gln Met Ala Arg Ala Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 6
<211> LENGTH: 36
<212> TYPE: PRT
<213> ORGANISM: Homo sapiens

<400> SEQUENCE: 6

Met Cys Met Pro Cys Phe Thr Thr Asp His Gln Met Ala Arg Arg Cys
1               5                   10                  15

Asp Asp Cys Cys Gly Gly Ala Gly Arg Gly Lys Cys Tyr Gly Pro Gln
            20                  25                  30

Cys Leu Cys Arg
        35
```